(12) United States Patent
Aarts et al.

(10) Patent No.: US 6,437,218 B1
(45) Date of Patent: Aug. 20, 2002

(54) DNA FRAGMENT ENCODING A PROTEIN INVOLVED IN FATTY ALDEHYDE DECARBONYLASE ACTIVITY, RECOMBINANT MOLECULES COMPRISING SAID FRAGMENT AND A METHOD FOR OBTAINING TRANSFORMED BACTERIAL CELLS AND PLANTS

(75) Inventors: Martinus Gerardus Maria Aarts, Wageningen; Andy Pereira, Ede; Wilhelmus Johannes Stiekema, Wageningen, all of (NL)

(73) Assignee: Centrum Voor Plantenver-Delings-En Reproduktie-Onderzoek, Droevendaalsesteeg (NL)

( * ) Notice: Subject to any disclaimer, the term of this patent is extended or adjusted under 35 U.S.C. 154(b) by 0 days.

(21) Appl. No.: 08/759,436

(22) Filed: Dec. 5, 1996

(30) Foreign Application Priority Data

Dec. 8, 1995 (EP) ............................ 95 203329

(51) Int. Cl.[7] ............................ A01H 5/00; C12N 1/21; C12N 5/04; C12N 15/29
(52) U.S. Cl. .................. 800/281; 800/278; 800/286; 800/295; 800/298; 536/23.1; 536/23.6; 536/24.1; 435/320.1; 435/69.1; 435/419; 435/252.3
(58) Field of Search ............... 536/23.1, 23.6, 536/24.1; 435/320.1, 172.3, 69.1, 419, 252.3; 800/205, 250, 281, 278, 286, 295, 298

(56) References Cited

U.S. PATENT DOCUMENTS 6,060,644 A * 5/2000 Schnable et al.

FOREIGN PATENT DOCUMENTS

WO 9218625 1/1992

OTHER PUBLICATIONS

Bowie et al. Science 247:1306–1310, 1990.*
Finnegan et al. Bio/Technology 12:883–888, Sep. 1994.*
Aarts, M. et al. "Molecular Characterization..." The Plant Cell, vol. 7, 2115–2127, Dec. 1995.
Larkin, JC et al. "Roles of The Glabrousi..." the Plant Cell, vol. 6, 1065–1076, Aug. 1994.
Lemieux, B. et al. "Epicuticular Wax and Eceriferum..." Cold Spring Harbor Laboratory Press vol. ARA Bidopsis, 1994 pp. 1031–1047.
M. Hulskamp, et al. "Identification of genes..." The Plant Journal, vol. 8, No. 5, Nov. 1995, 703–714.
Lemieux, B. et al. "GC–MS Analysis of the Wax..." Plant Physiol. Suppl. vol. 99, No. 1, May 1992, p. 14.
Newman, T. "Genes Galore: A Summary of Methods..." Plant Physiol. vol. 106, 1994, p. 1241.

* cited by examiner

*Primary Examiner*—Elizabeth Kemmerer
(74) *Attorney, Agent, or Firm*—Ladas & Parry

(57) ABSTRACT

This invention discloses a DNA fragment encoding a protein comprising the amino acid sequence depicted in FIG. 4 (SEQ ID NO:5), or a protein substantially homologous therewith and involved in fatty aldehyde decarbonylase activity. Said DNA fragment may have the nucleotide sequence depicted in FIG. 2 (SEQ ID NO:2) or a homologous nucleotide sequence. Further this invention discloses a promoter of said DNA fragment having the nucleotide sequence depicted in FIG. 3 (SEQ ID NO:4). Using said fragments transformed organisms can be produced showing an altered epicuticular wax composition.

32 Claims, 10 Drawing Sheets

FIGURE 1A

```
  1  GGTATAATGG CCACAAAACC AGGAGTCCTC ACCGATTGGC CTTGGACACC

51  CCTCGGAAGT TTCAAGGTGC ACTCTGTTTT CTTGTCCTTT AAATTTAAAA

101  AAACGCGTGC TTATGATCGA ATCCCGTTAC GTTACTGATA TATATGTTTT

151  TCTTGACATT GAAACAATAC ACAAGTACAT CGTAATAGCA CCATGGGCTG

201  TCCATAGCAC ATACAGGTTT GTGACAGATG TACCAGAGAA GAGGGATCTC

251  GGGTACTTCC TTGTGTTCCC ATTCTTGCTC TTCAGAATTC TGCACAACCA

301  GGTTTGGATC TCTCTGTCCC GTTACTATAC GTCCTCGGGA AAGAGACGCA

351  TCGTCGACAA GGGAATCGAC TTCAATCAGG TCGACAGGGA GACCAACTGG

401  TGCGCTTTTC TAAATTTTTA ACTACCTGCG TGCCTCGTGA GTATATGTAA

451  TCAACGTAAC TAATGAAATC CTGATATATG CGCAGGGATG ACCAAATATT

501  GTTCAACGGA GTGCTGTTCT ATATAGGCAT CAACCTATTG CCGGAGGCCA

551  AACAACTTCC CTGGTGGAGA ACTGACGGAG TGTTGATGGN NNNNNNNNNN

601  NNNNNNNNNN NNNNNNNNNN NNNNNNNNNN NNNNNNNNNN NNNNNNNNNN

651  NNNNNNNNNN NNNNNNNNNN NNNNNNNNNN NNNNNNNNNN NNNNNNNNNN

701  NNNNNNNNNN NNNNNNNNNN NNNNNNNNNN NNNNNNNNNN NNNNNNNNNN

751  NNNNNNNNNN NNNNNNNNNN NNNNAAAACG GCGTCAATAA TTTCGTTCGC

801  CGGATACATA ATCTACATAG ACTTCATGAA CAACATGGGA CACTGCAACT
```

FIGURE 1B

```
 851  TCGAGCTAAT CCCTAAGCGC CTTTTCCACC TCTTTCCTCC CCTCAAGTTC

901  CTCTGTTACA CCCCCTCGTA AGTCCTTAAT TAACAACTCC TCTTCTGTTT

951  CATACACTAC CAATTTGGCG TAGTAAAAGC ATTTACAAGA AACCATTCTT

1001  GATGATCTGA TACAAATACC TAGTTAGATC ATATTAATTA ATCCTCTTAT

1051  GGTCATCATA AAATCTAAGC AAATGATAAA TCATACTAAT ACAGGGGATA

1101  TATGCTATTA TAATAGAATT CCATACACGT ACTCCATTCC TGTATAAAAT

1151  AAAGGTGACG TGATACAGTT GTATGCTTAA TATGATCGTC AACTACTGAA

1201  TCCCTGGACC ACAACAGAAA AAAAAACAAT TATTTAATAT ATCTTACATG

1251  GTTCAACTTA TCGGCACATA ATCCAATTTC CCACAACTTT ACGCATTGAT

1301  AGCATCTTTA ACCAAACATC CTTTGAGAAC TATTTTAAAT ATCAAATTCA

1351  TTAGTCGATA TGTAGCAGGT GGTCCCTCTA AACGCTCAAG TTATATTAAA

1401  CCTTCTGGAT TCATATTTAC TTTTAAATAT TTGTGACTTT TTTTCCTTCG

1451  GTATTAATTT AGCGCAATGT GAAAGCAAAA TTTANTAGTT AAAATACATT

1501  AAAGTTTGGA TAATAAATGG AGCATGAGAA TTGCAGATAC CACTCGCTGC

1551  ACCACACGCA GTTCCGGACC AACTACTCCC TCTTCATGCC CTTGTATGAC

1601  TACATCTACG GCACAATGGA TGAAAGCACG GATACGTTGT ACGAGAAAAC

1651  TCTAGAAAGA GGAGATGATA TAGTGGACGT GGTGCACTTA ACTCACCTGA

1701  CGACGCCAGA ATC
```

FIGURE 2A

| | | |
|---|---|---|
| CGACGGTATA ATG GCC ACA AAA CCA GGA GTC CTC ACC GAT TGG CCT TGG<br>                Met Ala Thr Lys Pro Gly Val Leu Thr Asp Trp Pro Trp<br>                 1                    5                      10 | 49 |
| ACA CCC CTC GGA AGT TTC AAG TAC ATC GTA ATA GCA CCA TGG GCT GTC<br>Thr Pro Leu Gly Ser Phe Lys Tyr Ile Val Ile Ala Pro Trp Ala Val<br>     15                    20                    25 | 97 |
| CAT AGC ACA TAC AGG TTT GTG ACA GAT GAT CCA GAG AAG AGG GAT CTC<br>His Ser Thr Tyr Arg Phe Val Thr Asp Asp Pro Glu Lys Arg Asp Leu<br>    30                    35                    40                    45 | 145 |
| GGG TAC TTC CTT GTG TTC CCC TTC TTG CTC TTC AGA ATT CTG CAC AAC<br>Gly Tyr Phe Leu Val Phe Pro Phe Leu Leu Phe Arg Ile Leu His Asn<br>                 50                        55                        60 | 193 |
| CAG GTT TGG ATC TCT CTG TCC CGT TAC TAT ACG TCC TCG GGA AAG AGA<br>Gln Val Trp Ile Ser Leu Ser Arg Tyr Tyr Thr Ser Ser Gly Lys Arg<br>             65                     70                        75 | 241 |
| CGC ATC GTC GAC AAG GGA ATC GAC TTC AAT CAG GTC GAC AGG GAG ACC<br>Arg Ile Val Asp Lys Gly Ile Asp Phe Asn Gln Val Asp Arg Glu Thr<br>         80                    85                        90 | 289 |
| AAC TGG GAT GAC CAA ATA TTG TTC AAC GGA GTG CTG TTC TAT ATA GGC<br>Asn Trp Asp Asp Gln Ile Leu Phe Asn Gly Val Leu Phe Tyr Ile Gly<br>    95                    100                    105 | 337 |
| ATC AAC CTA TTG CCG GAG GCC AAA CAA CTT CCC TGG TGG AGA ACT GAC<br>Ile Asn Leu Leu Pro Glu Ala Lys Gln Leu Pro Trp Trp Arg Thr Asp<br>110                    115                    120                    125 | 385 |
| GGA GTG TTG ATG GCA GCG CTT ATT CAC ACC GGA CCG GTG GAG TTC CTC<br>Gly Val Leu Met Ala Ala Leu Ile His Thr Gly Pro Val Glu Phe Leu<br>                 130                        135                    140 | 433 |
| TAT TAT TGG CTC CAC AAA GCT CTC CAC CAT CAC TTT CTT TAT TCC CGC<br>Tyr Tyr Trp Leu His Lys Ala Leu His His His Phe Leu Tyr Ser Arg<br>             145                       150                       155 | 481 |
| TAC CAT TCC CAC CAC CAC TCC TCT ATC GTC ACT GAG CCC ATC ACT TCG<br>Tyr His Ser His His His Ser Ser Ile Val Thr Glu Pro Ile Thr Ser<br>         160                       165                    170 | 529 |
| GTG ATA CAT CCG TTT GCG GAG CAC ATA GCA TAC TTC ATC CTC TTC GCG<br>Val Ile His Pro Phe Ala Glu His Ile Ala Tyr Phe Ile Leu Phe Ala<br>     175                    180                    185 | 577 |
| ATA CCA CTA CTT ACC ACG TTG CTA ACA AAA ACG GCG TCA ATA ATT TCG<br>Ile Pro Leu Leu Thr Thr Leu Leu Thr Lys Thr Ala Ser Ile Ile Ser<br>190                    195                    200                    205 | 625 |
| TTC GCC GGA TAC ATA ATC TAC ATA GAC TTC ATG AAC AAC ATG GGA CAC<br>Phe Ala Gly Tyr Ile Ile Tyr Ile Asp Phe Met Asn Asn Met Gly His<br>                 210                        215                    220 | 673 |
| TGC AAC TTC GAG CTA ATC CCT AAG CGC CTT TTC CAC CTC TTT CCT CCC<br>Cys Asn Phe Glu Leu Ile Pro Lys Arg Leu Phe His Leu Phe Pro Pro<br>             225                       230                    235 | 721 |
| CTC AAG TTC CTC TGT TAC ACC CCC TCA TAC CAC TCG CTG CAC CAC ACG<br>Leu Lys Phe Leu Cys Tyr Thr Pro Ser Tyr His Ser Leu His His Thr<br>         240                       245                    250 | 769 |
| CAG TTC CGG ACC AAC TAC TCC CTC TTC ATG CCC TTG TAT GAC TAC ATC<br>Gln Phe Arg Thr Asn Tyr Ser Leu Phe Met Pro Leu Tyr Asp Tyr Ile<br>     255                    260                    265 | 817 |

FIGURE 2B

```
TAC GGC ACA ATG GAT GAA AGC ACG GAT ACG TTG TAC GAG AAA ACT CTA         865
Tyr Gly Thr Met Asp Glu Ser Thr Asp Thr Leu Tyr Glu Lys Thr Leu
270             275             280             285

GAA AGA GGA GAT GAT AGA GTG GAC GTG GTG CAC TTA ACT CAC CTG ACG         913
Glu Arg Gly Asp Asp Arg Val Asp Val Val His Leu Thr His Leu Thr
            290             295             300

ACG CCA GAA TCC ATA TAC CAT TTG CGC ATT GGC TTG GCC TCA TTT GCC         961
Thr Pro Glu Ser Ile Tyr His Leu Arg Ile Gly Leu Ala Ser Phe Ala
        305             310             315

TCC TAC CCC TTC GCT TAT AGA TGG TTC ATG CGC CTT TTG TGG CCT TTC        1009
Ser Tyr Pro Phe Ala Tyr Arg Trp Phe Met Arg Leu Leu Trp Pro Phe
    320             325             330

ACC TCT CTC TCC ATG ATA TTC ACG CTC TTC TAC GCC CGC CTC TTT GTC        1057
Thr Ser Leu Ser Met Ile Phe Thr Leu Phe Tyr Ala Arg Leu Phe Val
335             340             345

GCT GAG AGA AAC TCC TTC AAC AAG CTC AAC TTG CAG TCT TGG GTG ATA        1105
Ala Glu Arg Asn Ser Phe Asn Lys Leu Asn Leu Gln Ser Trp Val Ile
350             355             360             365

CCT AGA TAT AAT CTA CAG TAC TTG TTA AAA TGG AGG AAA GAA GCG ATC        1153
Pro Arg Tyr Asn Leu Gln Tyr Leu Leu Lys Trp Arg Lys Glu Ala Ile
            370             375             380

AAT AAC ATG ATT GAG AAA GCG ATA CTG GAG GCA GAT AAG AAA GGA GTG        1201
Asn Asn Met Ile Glu Lys Ala Ile Leu Glu Ala Asp Lys Lys Gly Val
        385             390             395

AAG GTG CTT AGT CTG GGT CTC ATG AAC CAA GGG GAG GAG CTT AAC AGG        1249
Lys Val Leu Ser Leu Gly Leu Met Asn Gln Gly Glu Glu Leu Asn Arg
    400             405             410

AAC GGA GAG GTG TAT ATC CAC AAC CAT CCA GAT ATG AAA GTG AGA CTG        1297
Asn Gly Glu Val Tyr Ile His Asn His Pro Asp Met Lys Val Arg Leu
415             420             425

GTC GAC GGC AGT AGA TTA GCA GCA GCT GTT GTG ATC AAC AGT GTA CCC        1345
Val Asp Gly Ser Arg Leu Ala Ala Ala Val Val Ile Asn Ser Val Pro
430             435             440             445

AAA GCA ACT ACA AGC GTC GTG ATG ACA GGC AAT CTC ACT AAG GTT GCC        1393
Lys Ala Thr Thr Ser Val Val Met Thr Gly Asn Leu Thr Lys Val Ala
            450             455             460

TAC ACC ATC GCC TCT GCT CTC TGC CAG AGA GGC GTT CAG GTC TCC ACT        1441
Tyr Thr Ile Ala Ser Ala Leu Cys Gln Arg Gly Val Gln Val Ser Thr
        465             470             475

CTG CGC CTA GAC GAG TAT GAG AAA ATA AGA TCA TGC GTT CCA CAA GAA        1489
Leu Arg Leu Asp Glu Tyr Glu Lys Ile Arg Ser Cys Val Pro Gln Glu
    480             485             490

TGC AGA GAC CAT TTG GTC TAT TTA ACC TCT GAA GCA CTC TCA TCA AAC        1537
Cys Arg Asp His Leu Val Tyr Leu Thr Ser Glu Ala Leu Ser Ser Asn
495             500             505

AAG GTA TGG CTG GTG GGA GAA GGA ACA ACA AGA GAA GAG CAG GAA AAA        1585
Lys Val Trp Leu Val Gly Glu Gly Thr Thr Arg Glu Glu Gln Glu Lys
510             515             520             525

GCC ACA AAA GGG ACA TTG TTT ATA CCA TTC TCA CAG TTC CCC CTC AAG        1633
Ala Thr Lys Gly Thr Leu Phe Ile Pro Phe Ser Gln Phe Pro Leu Lys
            530             535             540
```

FIGURE 2C

```
CAG TTA CGT AGC GAT TGT ATC TAT CAT ACC ACA CCA GCA TTG ATA GTT        1681
Gln Leu Arg Ser Asp Cys Ile Tyr His Thr Thr Pro Ala Leu Ile Val
            545             550                 555

CCA AAA TCT CTG GTG AAT GTC CAC TCC TGT GAG AAC TGG TTA CCG AGA        1729
Pro Lys Ser Leu Val Asn Val His Ser Cys Glu Asn Trp Leu Pro Arg
        560             565                 570

AAG GCG ATG AGT GCA ACT AGA GTG GCC GGC ATA TTG CAC GCC TTA GAA        1777
Lys Ala Met Ser Ala Thr Arg Val Ala Gly Ile Leu His Ala Leu Glu
    575             580                 585

GGA TGG GAA ACG CAT GAG TGT GGC ACA TCC CTT CTT CTC TCG GAT TTG        1825
Gly Trp Glu Thr His Glu Cys Gly Thr Ser Leu Leu Leu Ser Asp Leu
590             595                 600                 605

GAC AAA GTA TGG GAA GCC TGT CTC AGC CAC GGC TTC CAG CCT CTC CTC        1873
Asp Lys Val Trp Glu Ala Cys Leu Ser His Gly Phe Gln Pro Leu Leu
            610                 615                 620

CTT CCA CAT CAT TAAAACTCCA ACCTTGGAAG ATTTTTGGAG AATGAGAGCG            1925
Leu Pro His His
            625

ACACGCTCTG TGCTTCTTTT CCTTATGATC CAGCTCTTCC ACGCACACAT GAACTATGAA      1985

ACATATATAA AGCGCACACA TTTTATGTTT TACGCACACA TATATTTATG CATATCAAGC      2045

TTTTGGTGAT TATGGTATTG ATAGAGTCAA ATTAAGCTCG GTGACTATGG TATTAATAAG      2105

AGTACTATTT CCTTAAAAAA AAAAAAA                                          2132
```

FIGURE 3A

```
  1 CGTCAAGGTT TGTGAATATA TGAGGGAATT GGATATATAT ACTCAGCTTC

51 TCATATCAAA CAAAAAATAA TGTAGTAATG TGTATATATA GGTGGTCGTG

101 TTACGCGAGG AGGAACACAG CAAACTCATC AAATCTGGGG TTGACAAGAA

151 TCTGGTACTG TCTACAAGCA ATAGTTATTA CTCCCCAAAG GTGTGGTTGG

201 TGGGGGATGG AATAGAGAAC GAAGAGCAGA TGAAAGCAAA AGAAGGAACC

251 CTCTTTGTTC CCTTTTCTCA CTTTCCGCCC AACAAACTCC GCAAGGACTG

301 TTTCTACCAG TCCACTCCAG CTATGCGTGT CCCAAGTCT GCCCAAAACA

351 TCGACTCCTG TGAGGTACAT CTTTGAATTC TTATAGATAT ATCTGTAACT

401 TTTATATTAT ATAAGCTGAT AGATGTGTTC ATCTATAATG AATGAATGGT

451 TGTTATATAT ATATAGAACT GGCTGGGGAG GAGGGTGATG AGTGCATGGA

501 AAATAGGAGG TATAGTGCAT GCACTTGAGG GTTGGGAGGA GCATGACTGC

551 GGCAACACTT GCAACGTCCT CCGTCTCCAC GCCATATGGG AAGCTGCTCT

601 TCGCCATGAT TTCCAACCTC TCCCACCATC TCCTCTATGA GCTTTTTTCA

651 TATTCATACA TCTATGTCCC CTTTCTTGAT TATATCTACT TCCCTTCCAT

701 CATTGTTGCT GTTACTATGT TTTCTATCGA CAATATATAA GTACCCTTGT

751 TACCCTTGGT GCACGTGCTT CATATATGTT AGAAGGGCAA AAAATTCGTC

801 GTATGATATG CTTAGTTAAA TTTTATAAAA CTCAATAAAA ATCTTCAGAA
```

FIGURE 3B

```
 851 ACAGTGCTAT GATCATTACA TCTTAACTAA GTGATATATA TCTGCGTGCC

901 TATTTAACAA AATAAACAAA AAAACAAAAC AAAATATATT TGGGTGCATC

951 ATCAAATCAA AGTAGTTGCA AAAACTGGAC GAGGTTTTTA CTTAAATGGT

1001 CCTTACCCCG CATGGTCCAC TTGCTACCTA ATTAAGGATT GGTAGGGTGC

1051 GTATACGTAT ATAAATTGTG GCGGTGGGAG ATGGAGTTAC TAAAAACGAA

1101 ACGTACAAGT ATTATTCATA GCTCTCGTAT AAGGGGTTAG TCCTTAGATC

1151 TAGATATTTT CACTTTTCTT TCATTTATGT CGGAGCAACA GACACTAGCT

1201 GGCGCTTCAA CGTGCATGAT CTTGATTGGC TAGTAAATTC CAAGCATCAA

1251 TACCTAACAC ATGCCCAACT TGGTTCATTA GTATTCTTTC ATTGGTAAAA

1301 TACCCTTACC TTTCAATAAT ATCCAGAAAT AAATATATGA AGCCATCCAT

1351 CAACCGGTGC ATTTCCTCAA GGCATGGATA TGATATCAGA ACATCGATGA

1401 AGGTGGGAGG GGGTAATTAG CTGAGTGTCA TAAATGAGGA TCCATGTGGA

1451 GATCATCGAA TGGTAGTAGT ACATGTTTGG TCTTAGCTGG CCCCACCACA

1501 AGGAATTGGA CTGGTGGGAA GATAGGGGTG GGTTACGTCA TTCCACATAT

1551 CTACCAATTA AGGAGTTTAA TATAAACCTT GCTATATAAT GTACCTTGGC

1601 TCACAAGAGT TGAAGAGACA CAGTGACGAC ACAAACATAT TACA
```

```
CER1      1  MATKPGVLTDWPWTPLGSFKYIVIAPWAVHSTYRFVTDDP   40
SOLIPT    1                                      ...GDD    3

CER1     41  EKRDLGYFLVFPFLEFRILHNQVWISLSRYYTSSGKRRIV   80
SOLIPT    4  DLANNWCFHILVISELRFNLYHWYTNICNMLFLRNRRIE   43

CER1     81  DKGIDFNQVDRETNWDLQILFNGVLFYIGINLLPEAK-QL  119
SOLIPT   44  HQSIDFNQIDKEWNWDNFVILQALIASLAIYMFPQEFANL   83

CER1    120  PWWRTDGVTMAAEIHTGPVEFIYYWLHKALHHHFLYSRYH  159
SOLIPT   84  PVHKTKGLVAIVVIHVVVSEPLYYWLHRLLHTNVLFTPYH  123

CER1    160  SHHHSSIVTEPLTSVIHPFAEHIAYFILFAIPLLTTLETK  199
SOLIPT  124  SFHHSSAVPQPVTVGSTTFLEELLVTAVLGLPILGCSLSG  163

CER1    200  TASIISFAGYLLYIDFHNNMGHCNFSLIPKRFTHLFPPLK  239
SOLIPT  164  YGSKSIIYGYVLVFDFLRCLGHSNVEIHPHWIFDYFPFFR  203

CER1    240  FLCYIPSYHSLHHTQFRTNYISLFHPLYDYIYGTMDESTDT 279
SOLIPT  205  FIIYIPTYYSLHHSEMKSNYCLFMPLYDTMWNTLNTKSWG  243

CER1    280  LYEK-TLERGDD-RVDVVH-LTHLTTPESIYHLRIGLASF  316
SOLIPT  244  LHKKISLDSGKSTRVPDFVFLAHVVDITSALHVPFVERSP  283

CER1    317  ASYPEAYRWFMRLLWPFTSLSWIFTLFYARLFVAERNSFN  356
SOLIPT  284  SAMAYSARLFLLPLWPPTFAVMIVMWARSKTFLLSSYNLR  323

CER1    357  KLNLQSWVIPRYNLQYLLKWRKEAINNMIEKAILEADKKG  396
SOLIPT  324  GRLHQTWVVPREGFQYFLPEACQGINNHIEEAILRADKLG  363

CER1    397  VKVLSLGLMNQGEELNRNGEVYIHNHPDMKVRLVDGSRLA  436
SOLIPT  364  VKVISLAALNKNESLNRGGTLFVKKHPNLKVRVVHGNTLT  403
AT1001    1                 ...LNGSGEMYVQKYPKLKIRLVDGSSMA   26

CER1    437  AAVVINSVPKATTSVVMTGNLTKVAYTIASALCQRGVQVS  476
SOLIPT  404  AAVILNEINEDVKEVFLTGATSKLGRAIALYLCRRGVHVL  443
AT1001   27  ATVVINNIPKEATEIVFRGNLTKVASAVVFALCQKGVKVV   66

CER1    477  TLRL--DEYEKIRSCVPQECRDHLVYLTSE-ALSSNKVWL  513
SOLIPT  445  MLTLSTERFQNIQEEAPSKCRKNLVQVTKYQAAKNCKTWV  483
AT1001   67  VLRE--EEHSKLIKSGVE---KNLVLSTSN-SYYSPKVWL  100

CER1    514  VGEGTTREEQEKATKGTLFIPFSQPPLKQLRSDCIYHTTP  553
SOLIPT  484  IGKWITPGQQRWAPSGTHFHQFVVPPILAFRRTAPTETLP  523
AT1001  101  VGDGIENEEQMKAKEGTLFVPFSHFPNKLRKDCFYQSTP  138

CER1    554  ALIVPKSLVNVHSCENWLPRKAMSATRVAGILHALEGWET  593
SOLIPT  524  L
AT1001  139  AMRVPKSAQNIDSCENWLGRRVMSAWKIGGIVHALEGWEE  178

CER1    594  HFCGTSLLESDEDKVWEACLSHGFQPLLLPHH  625
AT1001  179  HDCGNTCNVLRLHAIWEAALRHDFQPLPPSPL  210
```

B

```
CER1      1  MATKPGVLTDWPWTPLGSFKYIVIAPWAVHSTYRFVTDDP   40
D15324       MASKPGPLTQWPWHNLGNYKYALVAPSAAYSTYRFVTASS
D22308       MATRPGPLTEWPWHRLGNFKYVVMAPVVAHGARRVHRNGW

CER1     41  E-KRDLGYFLVFPFLLFRILHNQVWISLSRYYTSSGKRRIV  80
D15324       RAERDLLNFMVFPHLLLRLLYGQLWITVSRHQTARSKEKIV  81
D22308       G-DLDIAFSLILPSLLLRMIHNQIWISLSRYQTARSKHRIV  80
```

FIGURE 4B

| | | | | | | | | | | | | | | |
|---|---|---|---|---|---|---|---|---|---|---|---|---|---|---|
|Met|Ala|Thr|Lys|Pro|Gly|Val|Leu|Thr|Asp|Trp|Pro|Trp|Thr|Pro|Leu|
|1| | |5| | | | |10| | | | |15| |

Met Ala Thr Lys Pro Gly Val Leu Thr Asp Trp Pro Trp Thr Pro Leu
1                5                      10                    15

Gly Ser Phe Lys Tyr Ile Val Ile Ala Pro Trp Ala Val His Ser Thr
              20              25                    30

Tyr Arg Phe Val Thr Asp Asp Pro Glu Lys Arg Asp Leu Gly Tyr Phe
            35              40                  45

Leu Val Phe Pro Phe Leu Leu Phe Arg Ile Leu His Asn Gln Val Trp
     50              55                  60

Ile Ser Leu Ser Arg Tyr Tyr Thr Ser Ser Gly Lys Arg Arg Ile Val
65              70              75                            80

Asp Lys Gly Ile Asp Phe Asn Gln Val Asp Arg Glu Thr Asn Trp Asp
            85                  90                    95

Asp Gln Ile Leu Phe Asn Gly Val Leu Phe Tyr Ile Gly Ile Asn Leu
           100              105                 110

Leu Pro Glu Ala Lys Gln Leu Pro Trp Trp Arg Thr Asp Gly Val Leu
        115              120                125

Met Ala Ala Leu Ile His Thr Gly Pro Val Glu Phe Leu Tyr Tyr Trp
130                 135                 140

Leu His Lys Ala Leu His His His Phe Leu Tyr Ser Arg Tyr His Ser
145                 150                 155                 160

His His His Ser Ser Ile Val Thr Glu Pro Ile Thr Ser Val Ile His
                165             170                 175

Pro Phe Ala Glu His Ile Ala Tyr Phe Ile Leu Phe Ala Ile Pro Leu
            180                 185                 190

Leu Thr Thr Leu Leu Thr Lys Thr Ala Ser Ile Ile Ser Phe Ala Gly
        195                 200                 205

Tyr Ile Ile Tyr Ile Asp Phe Met Asn Asn Met Gly His Cys Asn Phe
210                 215                 220

Glu Leu Ile Pro Lys Arg Leu Phe His Leu Phe Pro Pro Leu Lys Phe
225                 230                 235                 240

Leu Cys Tyr Thr Pro Ser Tyr His Ser Leu His His Thr Gln Phe Arg
            245                 250                 255

Thr Asn Tyr Ser Leu Phe Met Pro Leu Tyr Asp Tyr Ile Tyr Gly Thr
        260                 265                 270

Met Asp Glu Ser Thr Asp Thr Leu Tyr Glu Lys Thr Leu Glu Arg Gly
        275                 280                 285

Asp Asp Arg Val Asp Val Val His Leu Thr His Leu Thr Thr Pro Glu
        290                 295                 300

Ser Ile Tyr His Leu Arg Ile Gly Leu Ala Ser Phe Ala Ser Tyr Pro
305                 310                 315                 320

Phe Ala Tyr Arg Trp Phe Met Arg Leu Leu Trp Pro Phe Thr Ser Leu
            325                 330                 335

Ser Met Ile Phe Thr Leu Phe Tyr Ala Arg Leu Phe Val Ala Glu Arg
        340                 345                 350

FIGURE 4C

```
Asn Ser Phe Asn Lys Leu Asn Leu Gln Ser Trp Val Ile Pro Arg Tyr
    355                 360                 365
Asn Leu Gln Tyr Leu Leu Lys Trp Arg Lys Glu Ala Ile Asn Asn Met
    370                 375                 380
Ile Glu Lys Ala Ile Leu Glu Ala Asp Lys Lys Gly Val Lys Val Leu
385                 390                 395                 400
Ser Leu Gly Leu Met Asn Gln Gly Glu Glu Leu Asn Arg Asn Gly Glu
            405                 410                 415
Val Tyr Ile His Asn His Pro Asp Met Lys Val Arg Leu Val Asp Gly
            420                 425                 430
Ser Arg Leu Ala Ala Ala Val Val Ile Asn Ser Val Pro Lys Ala Thr
        435                 440                 445
Thr Ser Val Val Met Thr Gly Asn Leu Thr Lys Val Ala Tyr Thr Ile
    450                 455                 460
Ala Ser Ala Leu Cys Gln Arg Gly Val Gln Val Ser Thr Leu Arg Leu
465                 470                 475                 480
Asp Glu Tyr Glu Lys Ile Arg Ser Cys Val Pro Gln Glu Cys Arg Asp
            485                 490                 495
His Leu Val Tyr Leu Thr Ser Glu Ala Leu Ser Ser Asn Lys Val Trp
            500                 505                 510
Leu Val Gly Glu Gly Thr Thr Arg Glu Glu Gln Lys Ala Thr Lys
        515                 520                 525
Gly Thr Leu Phe Ile Pro Phe Ser Gln Phe Pro Leu Lys Gln Leu Arg
    530                 535                 540
Ser Asp Cys Ile Tyr His Thr Thr Pro Ala Leu Ile Val Pro Lys Ser
545                 550                 555                 560
Leu Val Asn Val His Ser Cys Glu Asn Trp Leu Pro Arg Lys Ala Met
            565                 570                 575
Ser Ala Thr Arg Val Ala Gly Ile Leu His Ala Leu Glu Gly Trp Glu
            580                 585                 590
Thr His Glu Cys Gly Thr Ser Leu Leu Leu Ser Asp Leu Asp Lys Val
        595                 600                 605
Trp Glu Ala Cys Leu Ser His Gly Phe Gln Pro Leu Leu Leu Pro His
    610                 615                 620
His
625
```

DNA FRAGMENT ENCODING A PROTEIN INVOLVED IN FATTY ALDEHYDE DECARBONYLASE ACTIVITY, RECOMBINANT MOLECULES COMPRISING SAID FRAGMENT AND A METHOD FOR OBTAINING TRANSFORMED BACTERIAL CELLS AND PLANTS

FIELD OF THE INVENTION

The present invention relates to a DNA fragment encoding a protein involved in fatty aldehyde decarbonylase activity, which protein is involved in the biosynthesis of alkanes. The invention also relates to a recombinant DNA containing the above fragment and to a method for obtaining transformed host cells using said recombinant DNA. The present invention further relates to transformed bacterial cells and to a method for producing a protein having fatty aldehyde decarbonylase activity using said transformed cells. Further, the invention relates to a method for obtaining a transformed plant showing an altered epicuticular wax composition and to a transformed plant, cell, fruit, seed of progeny derivable from said plant.

BACKGROUND OF THE ART

Plants are covered by an epicuticular wax (EW) layer composed of long chain lipids (C20–C40) consisting mostly of fatty acids, alcohols, esters and alkanes (Kolattukudy, 1976). There is a large variety of specific wax components which differ dramatically between plant species and thereby contribute towards the typical characteristics of the surface of individual plant species (Kolattukudy, 1975). This unique EW layer mediates the specific interactions of each plant species with its environment and is the first line of defense against abiotic and biotic stress, like drought/frost, pathogens and insects.

The primary function of the EW layer is to reduce water loss through the epidermis (Hall and Jones, 1961), a feature which contributes to drought tolerance. In addition individual lipid components or EW extracts and the physical structure of plant surface wax can influence insect behaviour which may lead to resistance of the plant to specific insects (Thompson, 1963, Städler, 1986, Eigenbrode and Espelie, 1995). Additionally the EW layer has a major function in the interaction of plants with plant pathogenic fungi (Podila et al., 1993). EW is also used by humans. The wax palm produces wax that is used for commercial purposes such as carnauba wax for polishing while similar types of waxes are collected from various other plant species.

The EW biosynthesis pathway has been suggested to be based on an elongation-reduction-decarboxylation mechanism which generates long chain fatty acids, aldehydes and alkanes (Bianchi et al., 1985; Lemieux et al., 1994; von Wettstein-Knowles, 1979; von Wettstein-Knowles, 1994). Thus, wax synthesis is determined by various biochemical steps suggesting that many genes are involved. This is in line with the large amount of mutant loci that have been observed for several species such as maize, barley, Brassica spp. and *Arabidopsis thaliana* (Baker, 1974; von Wettstein-Knowles, 1979; Bianchi et al., 1985; Kolattukudy, 1980; Koornneef et al., 1989; McNevin et al., 1993; Lemieux et al., 1994). Most of the mutants show a bright green wax-free phenotype compared to the glaucous appearance of wild type plants due to reduced wax production. Mutants are termed glossy (gl) for maize and Brassica spp. and eceriferum (cer) for barley and Arabidopsis. The natural gl and cer mutants, selected on visual and therefore wax structure basis, are dramatic mutants which have changes in lipid composition as well as crystal structure. In Brassica species, the gl mutants have been shown to be resistant to specific insects (Stoner, 1992).

The modification of the biosynthesis pathway of EW in plants by genetic engineering approaches will enable the modification of EW and consequently the interaction between the plant and its environment. Accordingly changes in the EW components will provide novel systems to engineer plants resistant to (a)biotic stress. In addition the modification of the biosynthesis route also opens the possibility to provide plants or bacteria with new waxes with industrial application including pharmaceuticals, cosmetics, detergents, plastics and lubricants.

In general the biochemical steps in Arabidopsis consist of a series of elongation reactions up to C30 chain fatty acids which can be either reduced to alcohols or reduced and decarbonylated to alkanes. Further analysis of the enzymes responsible for the formation of EW in plants has been hampered by the lack of purified enzymes involved in the EW biosynthesis. It is desirable therefore, for further study of the EW biosynthesis pathway to devise a strategy whereby these enzymes can be identified. The protein products encoded by CER genes are probably membrane bound and difficult to isolate biochemically. Therefore, in order to accomplish such isolation and to be able to modify the wax biosynthesis route, the object of this invention is to isolate the genes which encode the enzymes involved in EW biosynthesis.

To this end we analysed the cer mutants of *Arabidopsis thaliana* at the molecular level. *Arabidopsis thaliana* is particularly suited for the isolation of the genes involved in EW biosynthesis, especially as 22 loci affecting EW are already known (Koornneef et al., 1989; McNevin et al., 1993). Biochemical compositional analysis of these mutants has enabled functions to be attributed to many of the loci. By the application of the transposon tagging technology we were able to isolate a gene responsible for the synthesis of a protein which is involved in the decarbonylation of fatty aldehydes to alkanes. In conformity with the previous indication of the loci, the isolated gene is named CER1 gene and the corresponding protein is named CER1 protein (Aarts et al., 1993; Aarts et al., 1995).

Relevant Literature

A review on the biosynthesis and genetics of waxes in plants has been published by von Wettstein-Knowles (1995) in: Waxes, The Oily Press, Dundee, Scotland; Ed. J. R. Hamilton. A paper on the analysis of leaf epicuticular waxes of the Eceriferum mutants in Arabidopsis has been published by M. A. Jenks et al., 1995 in Plant Physiology, Volume 108, pages 369–377.

Eigenbrode and Espelie published a review on the effects of plant epicuticular lipids on insect herbivores in Annual Review of Entomology 1995, Volume 40 pages 171–194.

Definitions

Gene or sense gene: a nucleotide sequence that can be expressed as RNA molecule and/or polypeptide.

Promoter: a nucleotide sequence which directs the expression of a (sense-) gene or antisense gene, or nucleotide sequences derived thereof.

Antisense gene: a nucleotide sequence having a homology of more than 50%, preferably more than 80% with the target gene as defined herein, and which is linked to a promoter in 3' to 5' orientation with respect to the target gene and can be expressed as an RNA molecule.

Inhibitor gene: a (sense-) gene or antisense gene, expression of which leads to prevention or inhibition of the expression of a target gene as defined herein.

Target gene: a gene which activity is to be inhibited by proper expression of an inhibitor gene as defined herein.

SUMMARY OF THE INVENTION

The present invention describes the isolation of the CER1 gene involved in EW synthesis of *Arabidopsis thaliana*. The EW of cer1 mutants has been analysed previously and found to be especially rich in aldehydes while lacking alkanes. This shows that the CER1 protein encoded by the provided CER1 gene is involved in the conversion of aldehydes to alkanes.

The present inventors have isolated the CER1 gene from a genomic Arabidopsis thaliana DNA library in phage lambda which encodes a protein indicated as CER1 which is involved in EW synthesis, said gene having the nucleotide sequence as shown in FIG. 1 (SEQ ID NO:1). FIG. 1 shows the partial nucleotide sequence of the CER 1 gene, it being assumed that the complete nucleotide sequence will comprise about 6000 nucleotides. Further, the CER1 cDNA was isolated having the nucleotide sequence as shown in FIG. 2. (SEQ ID NO:2). The amino acid sequence of the CER1 protein deduced from said cDNA is shown in FIG. 4 (SEQ ID NO:5).

Accordingly, the present invention provides a DNA fragment encoding a protein comprising the amino acid sequence depicted in FIG. 4 (SEQ ID NO:5), or a protein substantially homologous therewith and involved in fatty aldehyde decarbonylase activity. Further the invention provides a DNA fragment comprising a nucleotide sequence depicted in FIG. 2 (SEQ ID NO:2), or a homologous nucleotide sequence. Said DNA fragment will hereinafter often be referred to as CER1 gene, it being understood that it is actually the CER1 cDNA. By "homologous nucleotide sequence" is intended any nucleic acid sequence that may be synthesized from the CER1 protein amino acid sequence, or alternatively identified in a different organism and isolated using CER1 protein nucleic acid sequences or antibodies prepared against the CER1 protein as probes. In this manner it can be seen that sequences that are isolated from other organisms using the CER1 sequences, either by nucleic acids or by antigenic methods, may similarly be used to isolate other proteins having the same activity. Such proteins are likewise considered as homologous.

Further, this invention provides the 5' regulatory region or promoter of the CER1 gene isolated from the chromosomal DNA of *Arabidopsis thaliana,* said promoter having the nucleotide sequence as shown in FIG. 3 (SEQ ID NO:4) or a promoter of a homologous gene.

Further, the invention provides recombinant DNA molecules (recombinant nucleic acid sequences) comprising a DNA fragment as defined above. In particular, the present invention provides recombinant nucleic acid sequences which can be suitably used for obtaining host cells showing altered fatty aldehyde decarbonylase activity essentially comprising a gene capable to (over)express the CER1 gene in said host cell, encoding the CER1 protein, said gene having the sequence as shown in FIG. 2 (SEQ ID NO:2) or a homologous gene. In particular host cells which contain the preferred substrates of the CER1 protein such as cells of Brassica plants are considered. In another preferred embodiment according to the invention the promoter that is driving the expression of said gene comprises the promoter of the CER1 gene, said promoter having the sequence as shown in FIG. 3 (SEQ ID NO:4).

The present invention also provides recombinant nucleic acid sequences which can be suitably used for obtaining host cells showing an altered fatty aldehyde decarbonylase activity essentially comprising an inhibitor gene capable of inhibiting expression of a target gene in the said host cell. In the preferred embodiment of the invention the target gene is the CER1 gene, said gene having the sequence as shown in FIG. 1 (SEQ ID NO:1) or a homologous target gene.

Further the present invention provides recombinant nucleic acid sequences which can be suitably used for obtaining a host cell showing an altered alkane biosynthesis, essentially comprising an inhibitor gene capable of inhibiting expression of a target gene encoding the CER1 protein involved in alkane biosynthesis in the said host cell, said target gene having the sequence as shown in FIG. 1 (SEQ ID NO:1) or a homologous target gene.

In the preferred embodiment of the invention the target gene is the CER1 gene having the sequence as shown in FIG. 1 (SEQ ID NO:1). In yet another preferred embodiment of the invention the inhibitor gene is a (sense-)gene or antisense gene directed against said target gene. In yet another preferred embodiment according to the invention the promoter that is driving the expression of the inhibitor gene comprises the promoter of the CER1 gene, said promoter having the sequence as shown in FIG. 3 (SEQ ID NO:4).

The present invention also provides a method for obtaining a plant with altered EW composition comprising the steps of:

a. transferring any recombinant nucleic acid sequence according to the invention to a plant cell, b. generating whole new plants from cells having incorporated said recombinant nucleic acid sequence, and c. selecting a plant that has an altered EW composition.

Yet another embodiment of the invention is a recombinant genome, comprising incorporated therein a recombinant nucleic acid sequence according to the invention. In particular a plant genome or a bacterial genome is considered. Generally, the invention provides a method for obtaining a transformed host cell by transferring a recombinant DNA molecule as defined above, to the host cell. Said recombinant DNA molecule preferably comprises a DNA fragment encoding the CER1 protein or a homologous protein, operably linked with a DNA sequence capable of effecting (over)expression of said DNA fragment in the host cell. In particular bacterial host cells are considered. The thus transformed bacterial cell can be used for the production of the CER1 protein or a homologous protein. Accordingly, the invention provides a method for producing a CER1 protein or a homologous protein, comprising culturing the transformed bacterial cell in a suitable culture medium and isolating the protein.

The invention further encompasses transformed plants and cells, fruit, seed or progeny derivable from said plants through crossing or selfing.

DESCRIPTION OF THE FIGURES

FIG. 1: Partial nucleotide sequence of the *Arabidopsis thaliana* CER1 gene (SEQ ID NO:1).

FIG. 2: Nucleotide sequence of the *Arabidopsis thaliana* CER1 cDNA (SEQ ID NO:2:). FIG. 2: Also shows the deduced amino acid sequence (SEQ ID NO:3:).

FIG. 3: Nucleotide sequence of the promoter of the *Arabidopsis thaliana* CER1 gene. (SEQ ID NO:3:)

FIG. 4: CER1 deduced amino acid sequence and comparison to homologous amino acid sequences.

(A) Amino acid sequence deduced from the CER1 cDNA (CER1), compared to the homologous amino acid sequences derived from the partial cDNA sequence of SOLIPTRB (SOLIPT) from *Senecio odorus*, and ATTS1001 (AT1001) from Arabidopsis. Two putative membrane spanning sequences in the CER1 amino acid sequence are overlined. A histidine rich motif is underlined. Putative glycosylated asparagine residues in the CER1 amino acid sequence are indicated (+) as well as the site of the target site duplication caused by insertion of I/dSpm89 (↓), that disrupts the reading frame in cer1::I/dSpm89 mutants. Dots indicate that the SOLIPTRB and ATTS1001 cDNAs are partial and that the N terminal ends of the complete amino acid sequences are missing (SEQ ID NO:3).

(B) N terminal stretch of about 80 amino acids with 37.5% identity overall between the CER1 protein and two amino acid sequences deduced from two rice cDNA clones (D15324 and D22308) Shaded boxes indicate similar amino acid residues, identical amino acid residues are indicated in bold face. Similar residues are grouped as follows: (V,L,I, M), (S,T), (Q,N,E,D), (K,R), (G,A) and (F,W,Y). The first 80 amino acids of SEQ ID NO:3 are shown in this figure.

(C) Amino acid sequence deduced from the CER1 cDNA (SEQ ID NO:5:).

DETAILED DESCRIPTION OF THE INVENTION

Isolation of the CER1 Gene of *Arabidopsis thaliana*
Phenotypic and Genetic Analysis of a Transposon Induced Cer Mutant To isolate genes involved in epicuticular wax biosynthesis, we used a I/dSpm transposon tagging approach to generate and screen Arabidopsis lines containing the En/Spm-I/dSpm transposon tagging system (See Experimental section; Aarts et al., 1995). Among the screened lines, we selected one line with multiple I/dSpm elements and the TEn2 transposase T-DNA (Aarts et al., 1995), which revealed some bright green semi-sterile mutants among normal wild type plants. Phenotypically these mutants strongly resembled a known class of cer mutants with a glossy stem and reduced fertility (Koornneef et al., 1989). Complementation tests with the cer1, cer3, cer6, and cer1) mutants in this class revealed that the transposon induced mutant was allelic to cer1-1. No clear phenotypic differences were found between our cer1 mutants (which we called cer1-m) and cer1-1 mutants. Both displayed a strong glossy stem and fruit phenotype, without any visible sign of wax production.

The Cer1-m Mutant is Tagged by an I/dSpm Element

The cer1-m mutant was found in a line with transposing I/dSpm elements and was presumably caused by insertion of an I/dSpm element. To determine whether cer1 was tagged, large offspring populations from mutants were screened for progeny that had reverted to the wild-type phenotype. This is a phenomenon typical of transposon-induced mutations. Germinal reversions were found at a frequency between 1 in 50 to 1 in 300 in four independent progenies, indicating that the unstable mutation was indeed due to a transposon insertion in the CER1 gene.

DNA blot analysis of segregating progenies (see Experimental section) revealed one I/dSpm insert (I/dSpm89) cosegregating with the cer1-m mutant phenotype. The flanking DNA of this I/dSpm89 insert was amplified by inverse polymerase chain reaction (IPCR) and cloned. Based on the DNA sequence, primers were designed for PCR amplification of wild-type and revertant I/dSpm89 excision alleles. Three independently derived germinal revertant plants all contained an excision allele, demonstrating that the cer1-m mutant was indeed tagged by the I/dSpm89 insertion, creating a cer1::I/dSpm89 allele. Excision of I/dSpm elements normally create short base pair deletions and additions (Aarts et al., 1993), but in these three cases, the DNA sequences of the revertant alleles were identical to the wild-type DNA sequence, suggesting insertion of I/dSpm89 at a vital position of the gene.

Cloning of the CER1 Gene

With the I/dSpm89 flanking genomic DNA as a probe, a homologous cDNA clone as well as a 17-kb long genomic clone was isolated from the respective DNA libraries. To confirm that the cDNA clone originated from the CER1 locus, part of the insert DNA was used as a probe and hybridized to a blot of cer1::I/dSpm89 mutant and revertant plants. All mutants were homozygous for a fragment containing the I/dSpm89 insert, although excision could be observed, and all revertants were either hemizygous for the I/dSpm89 insert or they lacked the insert.

Conclusive proof that the isolated gene was indeed the CER1 gene involved in epicuticular wax formation was obtained from the analysis of a plant with wild-type phenotype except for a small mutant cer sector. In the course of cer1::I/dSpm89 analysis three such plants were found in various progenies. The mutant sector in one of these plants, hemizygous for I/dSpm89, ended in a small leaf, from which DNA was isolated for PCR analysis. Combinations of an I/dSpm specific terminal primer and different CER1 specific primers (see Experimental section), were used for PCRs with DNA from the cer sector and from the wild- type rosette leaves of the same plant. Two cer sector-specific DNA fragments were amplified for two primer combinations. The new cer sector specific I/dSpm insertion was positioned within the coding region of the cloned gene, 1.0 kb upstream of the I/dSpm89 insert. As a new insertion of an I/dSpm element into the cloned gene, resulted again in a mutant cer phenotype we conclude that the cloned gene is indeed CER1 involved in epicuticular wax biosynthesis.

Analysis of the CER1 cDNA

Epicuticular waxes are mainly found on the stem and fruit epidermis of Arabidopsis and the isolated CER1 gene should be expressed in these organs. CER1 transcription was therefore tested by RNA gel blot hybridization and as expected, the CER1 transcript was found in wild-type stem and fruit tissue. Additional strong expression was detected in Arabidopsis flowers, in which expression of the CER1 gene could be expected based on the male sterile phenotype of the mutant. Arabidopsis has little wax formation on the leaves, explaining the low level of leaf transcript. Transcription of CER1 gene was blocked in cer1::I/dSpm89 mutant flowers, while the transcription in cer-1-1, flowers was not affected. The mutant phenotype of the chemically induced cer1-1 mutant is probably due to a minor rearrangement such as a point mutation. In flowers of the $F_1$ hybrid between cer1::I/dSpm and cer1-1, the transcription level of the gene was the intermediate of the two parents.

The 2109 bp long CER1 cDNA contained an open reading frame of 625 amino acids (FIG. 2). Part of the corresponding genomic DNA sequence was determined, and an in frame stop codon was found 33 bp upstream of the ATG start codon, indicating that the cDNA clone comprised the complete open reading frame. A putative TATA transcription initiation sequence was present 72 bp upstream of the ATG start codon in the genomic DNA sequence (FIG. 1). The predicted protein has an apparent molecular mass of 72.3 kD and a pI of 8.23. Analysis of the amino acid sequence with the PC/Gene computer package classifies the protein as an integral membrane protein. Two putative transmembrane helices are predicted stretching from amino acid positions 178 to 213 and 325 to 350, and additional membrane associated helices, cover amino acid positions 7–27, 45–65, 99–119 and 126–146. Two possible Asn glycosylation sites are found at positions 258 and 456. Insertion of I/dSpm89 disrupts the reading frame from Thr (amino acid position 272) onwards (FIG. 4).

FIG. 3 shows the nucleotide sequence of the promotor of the CER1 gene. Said sequence is obtained from *A. thaliana* ecotype Landsberg erecta genomic clone of the CER1 gene.

CER1 Homologs are Present in Other Species

Wax production is common to many plant species, and genes involved in wax biosynthesis may well be conserved among species. This was confirmed as database searches, carried out with the CER1 cDNA and predicted amino acid sequences, revealed significant homologies with cDNA and expressed sequence tag (EST) sequences from both dicot and monocot species (See Methods). The predicted amino acid sequence of the EST ATTS1001 cDNA isolated from flower buds of Arabidopsis, showed 53.8% identity to the C-terminal region (210 amino acids) of the predicted CER1 amino acid sequence (FIG. 4). In addition, a *B. campestris* flower bud EST was found with 49.1% predicted amino acid sequence identity (117 amino acids), a potato epidermal EST with 67.4% amino acid identity (46 amino acids), and a *Senecio odorus* epidermal cDNA with 31.3% amino acid identity (513 amino acids) (FIG. 4). This family of related sequences could be extended to monocot species maize and rice. A maize vegetative meristem EST showed 52.7% amino acid identity over 110 amino acids. The homology of two rice callus cDNAs sequenced from their 5' end, started exactly at the N terminus of the predicted CER1 amino acid sequence extending over the entire length of sequenced cDNA, representing about 80 amino acids (37.5% overall identity; FIG. 4). Interestingly, the predicted amino acid sequence of another rice cDNA with a short stretch of amino acid similarity to the predicted CER1 amino acid sequence, showed additional homology in this region to the C-5 sterol desaturase protein of yeast encoded by the ERG3 gene (Arthington et al., 1991). These two short stretches of homology are conserved between CER1, SOLIPTRB, the rice EST and ERG3, and a part of it is also found in the maize EST. Each stretch of homology reveals a short motif with the consensus sequence: Tyr-His-Ser/Thr-X-His-His (where X stands for any amino acid).

The CER1 Protein has a Function in Wax Alkane Biosynthesis

The cer1 mutant is one among four of the cer mutants with a drastically changed epicuticular wax phenotype, for which a biochemical function has been proposed to the corresponding wild-type gene. Biochemical studies led to the conclusion that CER2 and CER6 most likely encode components of fatty acid elongation, while CER4 is suggested to be involved in fatty aldehyde reduction (Hannoufa et al., 1993; Lemieux et al., 1994; Jenks et al., 1995). Biochemical studies (Hannoufa et al., 1993; McNevin et al., 1993; Lemieux et al., 1994) have shown that cer1 mutants are blocked in the conversion of stem wax $C_{30}$ aldehydes (triacontanal) to $C_{29}$ alkanes (nonacosane) and that they also lack the secondary alcohols (14- and 15-nonacosanol) and ketones (15-nonacosanone) derived thereof. Alkanes, secondary alcohols and ketones comprise around 65% of total wax in wild-type Landsberg erecta (Lemieux et al., 1994). The conversion of aldehydes to alkanes is moderated by aldehyde decarbonylases (Cheesbrough and Kolattukudy, 1984). We conclude that the CER1 protein is involved in this biochemical step to produce long chain alkanes.

Steps Towards Application

A nucleic acid sequence of the CER1 protein of this invention may be a DNA or RNA sequence, derived from genomic DNA, cDNA, mRNA or may be synthesized in whole or in part. The gene sequences may be cloned, for example, by isolating genomic DNA from an appropriate source, and amplifying and cloning the sequence of interest, using a polymerase chain reaction (PCR). Alternatively, the gene sequences may be synthesized, either completely or in part, especially where it is desirable to provide host-preferred sequences. Thus, all or a portion of the desired structural gene (that portion of the gene which encodes the CER1 protein) may be synthesized using codons preferred by a selected host. Host-preferred codons may be determined, for example, from the codons used most frequently in the proteins expressed in a desired host species.

The nucleic acid sequences associated with the CER1 protein will find many uses. For example, recombinant constructs can be prepared which can be used as probes or will provide for expression of the CER1 protein in host cells. Depending on the intended use, the constructs may contain the sequence which encodes the entire CER1 protein, or a portion thereof. For example critical regions of the CER1 protein such as the active site may be identified. Further constructs containing only a portion of the CER1 protein which encodes the amino acids necessary for a desired CER1 activity may thus be prepared.

Useful systems for the expression of the CER1 protein include prokaryotic cells, such as *E. coli,* yeast cells, and plant cells, both vascular and non-vascular plant cells being desired hosts. In this manner the CER1 protein may be produced. In addition site-specific mutagenesis of CER1 protein encoding sequences may be used to study effects of specific mutations on reactive properties of the CER1 protein. Additionally, antisense constructs may be prepared which provide for transcription of the complementary sequence of the CER1 protein encoding sequence or part thereof. In this manner, the amount of the CER1 protein produced in a target host organism can be reduced. Also the DNA sequence encoding the CER1 protein may be joined to other sequences such as sequences encoding a transit peptide for transport to the chloroplast.

The present invention envisages the following steps towards obtaining plants having altered waxes:

A sense-CER1 or antisense-CER1 gene of *Arabidopsis thaliana* or its homologous counterpart of other species is placed under the control of the CER1 promoter, which DNA sequence is shown in FIG. 3, and these constructs can be used for the transformation of fertile crop plants. After selection of transformed plants which express the construct, transgenic plants showing altered wax production can be selected.

In general plants showing altered wax synthesis can thus be obtained. Plants of a selected variety have to be genetically transformed by introducing into cells of the said plant one or more recombinant polynucleotides, essentially comprising one or more inhibitor genes, which upon proper expression in the plant, are capable of inhibiting expression of the CER1 gene.

Inhibition of the expression of the CER1 gene will result in plants showing altered wax composition. This can be accomplished by proper expression of an inhibitor gene directed against that target gene. Inhibitor genes can be suitably selected from a range of alternatives, including homologous or heterologous (i.e obtained from a different source) sense and antisense (synthetic)-genes or parts thereof with a suitable length and homology for proper inhibition, as illustrated in International Patent Application WO92/18625, and International Patent Application WO90/11682. Preferably the inhibitor gene is expressed in the epidermis according to the present invention. This can be accomplished by fusing the inhibitor gene under control of the promoter derived from the CER1 gene from *Arabidopsis thaliana* or its heterologous counterpart (i.e obtained from another source). In another preferred embodiment of the invention the CER1 protein encoding nucleic acid is joined to transcription initiation regulatory regions active in plants. Among these regions are regulatory regions associated with Agrobacterium genes (Nos, Ocs, Mas promoters) and viral genes (CaMV 35S, CaMV 19S promoters) or regulatory regions active in certain tissue such as those from napin, seed or leaf ACP, the small subunit of RUBISCO, Cab and the like. Regulatory transcription termination sequences may be provided in recombinant constructs of this invention as well. This may be the transcription termination region of the CER1 protein encoding gene or derived from a different gene source.

Plant transformation constructs accomodating the CER1 protein encoding gene may be employed with a wide variety of plants, especially plants which produce very long chain fatty aldehydes including but not limited to Brassica, maize and rice. This invention is applicable to monocotyledons and dicotyledons alike.

Transfer of recombinant nucleic acids into plants or parts thereof can be achieved by numerous techniques. Some of them are listed here as illustration and comprise transformation of protoplasts using the calcium/polyethylene glycol method (Krens et al. 1982; Negrutiu et al., 1987), electroporation (Shillito et al., 1985), microinjection (Crossway et al., 1986), (DNA or RNA coated) particle bombardment (Klein et al., 1987), infection with viruses and the like, natural DNA transfer by Agrobacterium species preferably by the use of the so-called binary vector system (Bevan et al., 1984). After identification of transformed plant material, whole plants are regenerated using well-known protocols described in literature (vide e.g. Horsch et al., 1985). There does not exist any restriction towards parts of the plants used. After transformed plants have been obtained, they can be evaluated for the presence of the desired trait and/or the degree to which the desired traits are expressed. A first evaluation may include the level of expression of the inhibitor gene and the extent to which the transgenic plants show altered wax biosynthesis. Subsequently transgenic plants can be selected that show stable and/or predictable inheritance of the trait, and the like. The present invention can be applied in any plant capable of wax biosynthesis, for which the production of altered waxes is of commercial interest.

The present invention also envisages the expression of the CER1 protein in microorganisms. For expression in eukaryotic or procaryotic microorganisms, particular unicellular hosts, a wide variety of constitutive or regulatable promoters may be employed. Expression in microorganisms can provide a ready source of the CER1 protein. Among transcriptional initiation regions which have been described are regions from bacterial and yeast hosts, such as *E. coli, B. subtilis, Sacchromyces cerevisae,* including genes such as beta-galactosidase, T7 polymerase, tryptophan E and the like.

Experimental

Methods

Enhancer/Suppressor_Mutator-Inhibitor/defective Suppressor_Mutator Transposon Plants and Eceriferum Mutants All experiments were carried out with the Landsberg erecta ecotype of *Arabidopsis thaliana*, which was also the genetic background of the chemically or physically induced eceriferum (cer) mutants tested for phenotypic complementation (all mutants provided by M. Koornneef, Wageningen Agricultural University). For screening, 25 Enhancer/Suppressor_mutator-Inhibitor/defective Suppressor_mutator (En/Spm-I/dSpm) transposon tagging lines with 12 plants each, were grown individually in the greenhouse and examined for cer mutations. All lines were obtained after two generations of self-pollination, starting with one plant containing the TEn2 En/Spm transposase T-DNA locus along with several transposed I/dSpm elements (Aarts et al., 1995). The original cer1::I/dSpm89 transposon tagged mutant was found in line H12.1.1.6.2, containing about 15 different I/dSpm elements and homozygous for the TEn2 T-DNA. TEn5 is another En/Spm transposase line containing a different, more active T-DNA locus and no other I/dSpm elements. This line was crossed to a cer1::I/dSpm89 plant and cer1F$_2$ plants were screened for excision sectors. All plants grown for progeny were kept in Aracon containers (BetaTech, Gent, Belgium) to prevent cross-pollination. Fertility of cer mutants was conditioned by keeping the plants enclosed in a plastic bag to increase relative humidity (Koornneef et al., 1989).

Identification of a Cer1-m Cosegregating I/dSpm Element and Isolation of Flanking Genomic DNAs The original cer1-m mutant was back-crossed to Landsberg erecta wild type for two generations. Genomic DNA was isolated from second backcross offspring plants, and tested for the presence of I/dSpm elements. All plants were allowed to self and their progeny was tested for segregation of the cer1 phenotype to confirm linkage of an I/dSpm element with the cer1 phenotype in the second backcross offspring. Genomic DNA from plants containing the cer1-linked I/dSpm89 element and a few other unlinked I/dSpm elements was used to obtain DNA flanking both sides of I/dSpm89 after I/dSpm specific inverse PCR (IPCR; Masson et al.; 1991). Additional PCR amplification using primer T (5'-GACACTCCTTAGATCTTTTCTTGTAGTG-3') (SEQ ID NO:12) fitting both terminal inverted repeats of I/dSpm enabled the isolation of fragments with minimal transposon DNA. Based on I/dSpm89 flanking sequences, primers 2 and 3 (5'-GGAGCATGAGAATTGCAGATACC-3' (SEQ ID NO:7) and 5'-GGCGTCGTCAGGTGAGTTAAGTGC-3') (SEQ ID NO:8) were designed which amplified a 189-bp wild-type DNA fragment covering the I/dSpm89 insertion site.

cDNA and Genomic Library Screening

An amplified cDNA lambda library representing different Arabidopsis tissues (Newman et al., 1994) and a Landsberg erects genomic library obtained through the Arabidopsis Biological Resource Center (Ohio State University, Columbus, Ohio) and the European DNA Resource Centre (Max-Delbrück Laboratory, Köln, Germany), were screened with the I/dSpm89 IPCR fragment probe. The DNA insert of the genomic clone was subcloned as EcoRI fragments.

DNA and RNA Analysis

DNA and RNA gel blots were standardly hybridized at 65° C. overnight and washed twice at 65° C. with 2×SSC (1×SSC is 0.15 M NaCl, 0.015 M sodium citrate), 1% SDS or (more stringently) with 0.1×SSC, 1% SDS. DNA sequences were determined using an ABI Sequencer. CER1 cDNA SalI and SalI-XbaI fragments were subcloned in pBluescript SK$^+$ and sequenced. The double-stranded DNA sequence was completed using cDNA specific primers 1 (5'-GGCCTCCGGCAATAGGTTGATG-3'), (SEQ ID NO:6) 4 (5'-GGTGCTTAGTCTGGGTCTCATG-3') (SEQ ID NO:9), 5 (5'-CACAGGAGTGGACATTCACCAGAG- 3') (SEQ ID NO:10) and 6 (5'-CGCATGAGTGTGGCACATCCC-3') (SEQ ID NO:11) (Isogen Bioscience, Amsterdam). The same primers as well as primers 2 and 3 flanking I/dSpm89 were used to test for a new insertion in CER1 causing the mutant cer1 sector in combination with the I/dSpm terminal inverted repeats primer IT; FIG. 4). PCR conditions for primers 1 to 6 and T are 5 min at 94° C., followed by 30 cycles of 94° C. (30 sec), 55° C. (30 sec) and 72° C. (3 min.). In addition to the cDNA sequence, the sequence of a single strand of genomic DNA up to 1656 bp upstream of the CER1 start codon was determined.

The cDNA sequence and the predicted amino acid sequence were analysed using the PC/Gene computer package (IntelliGenetics, Geneva, Switzerland).

Data Base Searches

GenBank and EST data bases were searched for CER1 homologs using BLAST programs (Altschul et al., 1990). GenBank accession numbers of the reported homologous sequences are: L33792 for the *Senecio odorus* SOLIPTRB partial cDNA; T22420 and Z18418 for two Arabidopsis ESTs with nearly 100% identity to the CER1 cDNA; Z25487 for the Arabidopsis ATTS1001 EST; L35835 for the Brassica campestris EST; R27543 for the potato EST; T70657 for the maize EST; D15324 and D22308 for two rice ESTs with N-terminal homology to CER1; D40658 and D23996 for two rice ESTs with internal homology. The cDNA clones corresponding with the four rice ESTs have been kindly obtained from Yoshiaki Nagamura of the Rice Genome Research Program (STAFF Institute, Ibaraki, Japan). The 5' ends of both D15324 and D22308 have been resequenced to correct for frameshifts and other occassional misreadings found in the original data base sequence.

REFERENCES

Aarts, M. G. M., Dirkse, W. G., Stiekema, W. J., and Pereira, A. (1993). Transposon tagging of a male sterility gene in Arabidopsis. Nature 363, 715–717.

Aarts, M. G. M., Corzaan, P., Stiekema, W. J., and Pereira, A. (1995). A two-element *Enhancer-Inhibitor* transposon system in *Arabidopsis thaliana* . Mol. Gen. Genet. 247, 555–564.

Altschul, S. F., Gish, W., Miller, W., Myers, E. W., and Lipman, D. J. (1990). Basic local alignment search tool. J. Mol. Biol. 215, 403–410.

Arthington, B. A., Bennet, L. G., Skatrud, P. L., Guynn, C. J., Barbuch, R. J., Ulbright, C. E., and Bard, M. (1991). Cloning, disruption and sequence of the gene encoding yeast C-5 sterol desaturase. Gene 102, 39–44.

Baker, E. A. (1974). The influence of environment on leaf wax development in *Brassica oleracea* var. *gemmifera*. New Phytol. 73, 955–966.

Bevan, M. A. (1984) Binary Agrobacterium vectors for plant transformation. Nucl Acids Res. 12, 8711–8712.

Bianchi, A., Bianchi, G., Avato, P., and Salamini, F. (1985). Biosynthetic pathways of epicuticular wax of maize as assessed by mutation, light, plant age and inhibitor studies. Maydica 30, 179–198.

Cheesbrough, T. M., and Kolattukudy, P. E. (1984). Alkane biosynthesis by decarbonylation of aldehydes catalyzed by a particulate preparation from *Pisum sativum*. Proc. Natl. Acad. Sci. USA 81, 6613–6617.

Crossway, A., Oakes, J. V., Irvine, J. M., Ward, B., Knauf, V. C., Shewmaker, C. K. (1986) Integration of foreign DNA following microinjection of tobacco mesophyll protoplasts. Mol. Gen. Genet. 202, 179–185.

Eigenbrode, S. D., and Espelie, K. E. (1995). Effects of plant epicuticular lipids on insect herbivores. Annu. Rev. Entomol. 40, 171–194.

Goldberg, R. B., Beals, T. P., and Sanders, P. M. (1993). Anther development: Basic principles and practical applications. Plant Cell 5, 1217–1229.

Hall, D. M., and Jones, R. L. (1961). Physiological significance of surface wax on leaves. Nature 191, 95–96.

Hannoufa, A., McNevin, J., and Lemieux, B. (1993). Epicuticular waxes of eceriferum mutants of *Arabidopsis thaliana* . Phytochemistry 33, 851–855.

Horsch, R. B., Fry, J. E., Hoffmann, N. L., Eichholtz, D., Rogers, S. G., Fraley, R. T. (1985) A simple and general method for tranferring genes into plants. Science 227, 1229–1231.

Jenks, M. A., Tuttle, H. A., Eigenbrode, S .D., and Feldmann, K. A. (1995). Leaf epicuticular waxes of the eceriferum mutants in Arabidopsis. Plant Physiol. 108, 369–377.

Klein, T. M., Wolf, E. D., Wu, R., Sanford, J. C. (1987) High-velocity microprojectiles for delivering nucleic acids into living cells. Nature 327, 70–73.

Kolattukudy, P. E. (1975). Biochemistry of cutin, suberin and waxes, the lipid barriers on plants. In Recent Advances in the Chemistry and Biochemistry of Plant Lipids, T. Galliard and E. I. Mercer, eds (New York: Academic Press), pp 203–246.

Kolattukudy, P. E. (ed) (1976). Chemistry and Biochemistry of Natural Waxes. (Amsterdam: Elsevier).

Kolattukudy, P. E. (1980). Cutin, suberin and waxes. In The Biochemistry of Plants, vol 4, Lipids: Structure and Function, P. K. Stumpf, ed (New York: Academic Press), pp 571–645.

Koornneef, M., Hanhart, C. J., and Thiel, F. (1989). A genetic and phenotypic description of eceriferum (cer) mutants in *Arabidopsis thaliana* . J. Heredity 80, 11 8–122.

Krens, F. A., Molendijk, L., Wullems, G. J., Schilperoort, R. A. (1982) In vitro transformation of plant protoplasts with Ti-plasmid DNA. Nature 296, 72–74.

Lemieux, B., Koornneef, M., and Feldmann, K. A. (1994). Epicuticular wax and eceriferum mutants. In Arabidopsis, E. M. Meyerowitz and C. R. Somerville, eds (Cold Spring Harbor, N.Y.: Cold Spring Harbor Laboratory Press), pp 1031–1047.

Masson, P., Strem, M., and Fedoroff, N. (1991). The tnpA and tnpD gene products of the Spm element are required for transposition in tobacco. Plant Cell 3, 73–85.

McNevin, J. P., Woodward, W., Hannoufa, A., Feldmann, K. A., and Lemieux, B. (1993). Isolation and characterization of eceriferum (cer) mutants induced by T-DNA insertions in *Arabidopsis thaliana*. Genome 36, 610–618.

Negrutiu, I., Mouras, A., Horth, M., Jacobs, M. (1987) Direct gene transfer to plants: Present developments and some future prospectives. Plant Physiol. Biochem. 25, 493–503.

Newman, T., de Bruijn, F. J., Green, P., Keegstra, K., Kende, H., McIntosh, L., Ohirogge, J., Raikhel, N., Somerville, S., Thomashow, M., Retzel, E., and Somerville, C. (1994). Genes galore: A summary of methods for accessing results from large-scale partial sequencing of anonymous Arabidopsis cDNA clones. Plant Physiol. 106, 1241–1255.

Podila, G. K., Rogers, L. M., and Kolattukudy, P. E. (1993). Chemical signals from avocado surface wax trigger germination and appressorium formation in *Colletotrichum gloeosporioides*. Plant Physiol. 103, 267–272.

Shillito, R. D., Saul, M. W., Paszkowski, J., Müller, M., Potrykus, 1. (1985) High frequency direct gene transfer to plants. Bio/Technology 3, 1099–1103.

Städler, E. (1986). Oviposition and feeding stimuli in leaf surface waxes. In Insects and the Plant Surface. B. Juniper and R. Southwood, eds (London: Edward Arnold), pp 105–121.

Stoner K. A. (1992). Density of imported cabbageworms, cabbage aphids, and flea beetles on glossy and trichome-bearing lines of Brassica oleraceae L. J. Econ. Entom. 85: 1023–1030.

Thompson, K. F. (1963). Resistance to the cabbage aphid (*Brevicoryne brassicae*) in *Brassica brasicae*) plants. Nature 198, 209.

von Wettstein-Knowles, P. (1979). Genetics and biosynthesis of plant epicuticular waxes. In Advances in the Biochemistry and Physiology of Plant Lipids, L.-Å. Appelqvist and C. Liljenberg, eds (Amsterdam: Elsevier/North-Holland Biomedical Press), pp 1–26.

von Wettstein-Knowles, P. (1994). Biosynthesis and genetics of waxes. In Waxes: Chemistry, Molecular Biology and Functions. R. J. Hamilton, ed (Dundee, UK: The Oily Press). pp 91–129.

What is claimed is:

1. An isolated and purified DNA fragment encoding a protein comprising the amino acid sequence depicted in FIG. 4C (SEQ ID NO:5).

2. An isolated and purified DNA fragment comprising a nucleotide sequence selected from the group consisting of:
    a) a nucleotide sequence depicted in FIG. 2 (SEQ ID NO:2);
    b) a nucleotide sequence encoding a fragment of the amino acid sequence depicted in FIG. 4C (SEQ ID NO: 5) having activity for converting aldehydes to alkanes in the epicuticular wax biosynthesis pathway; and
    c) a nucleotide sequence encoding a protein which converts aldehydes to alkanes in the epicuticular wax biosynthesis pathway which protein is encoded by a nucleotide sequence which hybridizes to the nucleotide sequence depicted in FIG. 2 (SEQ ID NO:2) at 65° C. in 2×SSC and 1% SDS.

3. An isolated and purified DNA sequence comprising a promoter of the DNA fragment as defined in claim 2 said promoter having the nucleotide sequence depicted in FIG. 3 (SEQ ID NO:4).

4. An isolated and purified DNA molecule comprising a DNA fragment of claim 2.

5. An isolated and purified DNA molecule according to claim 4 in which the DNA fragment is operably linked with a DNA sequence which effects expression of said DNA fragment in a host cell.

6. An isolated and purified DNA molecule according to claim 4 in which the DNA fragment is operably linked with a DNA sequence which effects overexpression of said DNA fragment in a host cell.

7. An isolated and purified DNA molecule according to claim 5 in which the DNA sequence driving the expression of said DNA fragment is a promoter having the nucleotide sequence depicted in FIG. 3 (SEQ ID NO:4) or a heterologous promoter.

8. An isolated and purified DNA molecule comprising:
    a) an antisense gene capable of inhibiting the expression of a target gene in a plant host cell, which target gene is present in the plant host cell and comprises the DNA fragment as defined in claim 2; and
    b) a DNA sequence which effects expression of the antisense nucleotide sequence in the host cell, operably linked to the antisense nucleotide sequence.

9. An isolated and purified DNA molecule according to claim 8 in which the DNA sequence which effects expression of the antisense nucleotide sequence is a promoter as depicted in FIG. 3 (SEQ ID NO:4) or a heterologous promoter.

10. A method for obtaining a transformed host cell by transferring a DNA molecule of claim 5 to a bacterial host cell.

11. A method for obtaining a transformed host cell by transferring a DNA molecule of claim 7 to a bacterial host cell.

12. A method for obtaining a transformed host cell by transferring a DNA molecule of claim 8 to a bacterial host cell.

13. A transformed bacterial cell obtained by the method of claim 10.

14. A transformed bacterial cell obtained by the method of claim 11.

15. A transformed bacterial cell obtained by the method of claim 12.

16. A method for producing a protein comprising the amino acid sequence depicted in FIG. 4C (SEQ ID NO:5) or a protein which is encoded by a nucleotide sequence which hybridizes to the nucleotide sequence of SEQ ID NO:2 at 65° C. in 2×SSC and 1% SDS which comprises culturing a transformed bacterial cell according to claim 13 in a culture medium and isolating the protein.

17. A method for obtaining a transformed plant showing an altered epicuticular wax (EW) composition comprising the steps of:
    a) transferring a DNA molecule as defined in claim 5 to a plant cell,
    b) generating whole plants from cells having incorporated said DNA molecule and
    c) selecting a plant showing an altered EW composition.

18. A method for obtaining a transformed plant showing an altered epicuticular wax (EW) composition comprising the steps of:
    a) transferring a DNA molecule as defined in claim 7 to a plant cell, b) generating whole plants from cells having incorporated said DNA molecule and c) selecting a plant showing an altered EW composition.

19. A method for obtaining a transformed plant showing an altered epicuticular wax (EW) composition comprising the steps of:

a) transferring a DNA molecule as defined in claim 8 to a plant cell, b) generating whole plants from cells having incorporated said DNA molecule; and c) selecting a plant showing an altered EW composition.

20. A method for obtaining a transformed plant showing an altered epicuticular wax (EW) composition comprising the steps of:

a) transferring a DNA molecule as defined in claim 9 to a plant cell, b) generating whole plants from cells having incorporated said DNA molecule; and c) selecting a plant showing an altered EW composition.

21. A transformed plant obtained by the method of claim 17.

22. A transformed plant obtained by the method of claim 18.

23. A transformed plant obtained by the method of claim 19.

24. A transformed plant obtained by the method of claim 20.

25. A cell, fruit, seed or progeny of the plant according to claim 21.

26. A cell, fruit, seed or progeny of the plant according to claim 22.

27. A cell, fruit, seed or progeny of the plant according to claim 23.

28. A cell, fruit, seed or progeny of the plant according to claim 24.

29. A method of introducing a nucleic acid into a plant cell, which method comprises the steps of:

(a) inserting into a plant cell (i) a sense nucleic acid, wherein said sense nucleic acid encodes a product of a cuticular lipid gene to be expressed in said plant cell, or (ii) an antisense nucleic acid wherein said antisense nucleic acid expresses an antisense nucleic acid molecule, which is specific for mRNA or a portion thereof of a cuticular lipid gene present in and expressed in said plant cell, wherein said antisense nucleic acid molecule is of sufficient length to inhibit expression of said cuticular lipid gene, wherein said sense or antisense nucleic acid is operatively linked to one or more regulatory sequences, and wherein said cuticular lipid gene comprises a sequence selected from the group consisting of SEQ ID NO: 2, and a sequence which hybridizes to SEQ ID NO: 2 at 65° C. in 2×SSC and 1% SDS;

(b) expressing said sense or antisense nucleic acid in said plant cell; and (c) culturing said plant cell.

30. The method of claim 29, further comprising the step of:

(d) generating from the plant cell a plant.

31. A transformed plant obtained by the method of claim 29.

32. A cell, fruit, seed or progeny of the plant according to claim 29.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 1713 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Arabidopsis thaliana
      (B) STRAIN: Landsberg erecta ecotype (vii) IMMEDIATE SOURCE:
      (A) LIBRARY: Coates (viii) POSITION IN GENOME:
      (A) CHROMOSOME/SEGMENT: 1
      (B) MAP POSITION: 12
      (C) UNITS: cM (x) PUBLICATION INFORMATION:
      (A) AUTHORS: Aarts, Mark G.M.
          Stiekema, Willem J.
          Pereira, Andy (xi) SEQUENCE DESCRIPTION: SEQ ID NO: 1:

```
GGTATAATGG CCACAAAACC AGGAGTCCTC ACCGATTGGC CTTGGACACC CCTCGGAAGT      60

TTCAAGGTGC ACTCTGTTTT CTTGTCCTTT AAATTTAAAA AAACGCGTGC TTATGATCGA     120

ATCCCGTTAC GTTACTGATA TATATGTTTT TCTTGACATT GAAACAATAC ACAAGTACAT     180

CGTAATAGCA CCATGGGCTG TCCATAGCAC ATACAGGTTT GTGACAGATG TACCAGAGAA     240

GAGGGATCTC GGGTACTTCC TTGTGTTCCC ATTCTTGCTC TTCAGAATTC TGCACAACCA     300

GGTTTGGATC TCTCTGTCCC GTTACTATAC GTCCTCGGGA AAGAGACGCA TCGTCGACAA     360

GGGAATCGAC TTCAATCAGG TCGACAGGGA GACCAACTGG TGCGCTTTTC TAAATTTTTA     420

ACTACCTGCG TGCCTCGTGA GTATATGTAA TCAACGTAAC TAATGAAATC CTGATATATG     480

CGCAGGGATG ACCAAATATT GTTCAACGGA GTGCTGTTCT ATATAGGCAT CAACCTATTG     540

CCGGAGGCCA AACAACTTCC CTGGTGGAGA ACTGACGGAG TGTTGATGGN NNNNNNNNNN     600

NNNNNNNNNN NNNNNNNNNN NNNNNNNNNN NNNNNNNNNN NNNNNNNNNN NNNNNNNNNN     660

NNNNNNNNNN NNNNNNNNNN NNNNNNNNNN NNNNNNNNNN NNNNNNNNNN NNNNNNNNNN     720
```

-continued

```
NNNNNNNNNN NNNNNNNNNN NNNNNNNNNN NNNNNNNNNN NNNNNNNNNN NNNNAAAACG       780

GCGTCAATAA TTTCGTTCGC CGGATACATA ATCTACATAG ACTTCATGAA CAACATGGGA       840

CACTGCAACT TCGAGCTAAT CCCTAAGCGC CTTTTCCACC TCTTTCCTCC CCTCAAGTTC       900

CTCTGTTACA CCCCCTCGTA AGTCCTTAAT TAACAACTCC TCTTCTGTTT CATACACTAC       960

CAATTTGGCG TAGTAAAAGC ATTTACAAGA AACCATTCTT GATGATCTGA TACAAATACC      1020

TAGTTAGATC ATATTAATTA ATCCTCTTAT GGTCATCATA AAATCTAAGC AAATGATAAA      1080

TCATACTAAT ACAGGGGATA TATGCTATTA TAATAGAATT CCATACACGT ACTCCATTCC      1140

TGTATAAAAT AAAGGTGACG TGATACAGTT GTATGCTTAA TATGATCGTC AACTACTGAA      1200

TCCCTGGACC ACAACAGAAA AAAAAACAAT TATTTAATAT ATCTTACATG GTTCAACTTA      1260

TCGGCACATA ATCCAATTTC CCACAACTTT ACGCATTGAT AGCATCTTTA ACCAAACATC      1320

CTTTGAGAAC TATTTTAAAT ATCAAATTCA TTAGTCGATA TGTAGCAGGT GGTCCCTCTA      1380

AACGCTCAAG TTATATTAAA CCTTCTGGAT TCATATTTAC TTTTAAATAT TTGTGACTTT      1440

TTTTCCTTCG GTATTAATTT AGCGCAATGT GAAAGCAAAA TTTANTAGTT AAAATACATT      1500

AAAGTTTGGA TAATAAATGG AGCATGAGAA TTGCAGATAC CACTCGCTGC ACCACACGCA      1560

GTTCCGGACC AACTACTCCC TCTTCATGCC CTTGTATGAC TACATCTACG GCACAATGGA      1620

TGAAAGCACG GATACGTTGT ACGAGAAAAC TCTAGAAAGA GGAGATGATA TAGTGGACGT      1680

GGTGCACTTA ACTCACCTGA CGACGCCAGA ATC                                  1713
```

(2) INFORMATION FOR SEQ ID NO: 2:

(i) SEQUENCE CHARACTERISTICS:
      (A) LENGTH: 2132 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Arabidopsis thaliana
      (B) STRAIN: Landsberg erecta ecotype (vii) IMMEDIATE SOURCE:
      (A) LIBRARY: Coates (viii) POSITION IN GENOME:
      (A) CHROMOSOME/SEGMENT: 1
      (B) MAP POSITION: 12
      (C) UNITS: cM (ix) FEATURE:
      (A) NAME/KEY: CDS
      (B) LOCATION:11..1885

(x) PUBLICATION INFORMATION:
      (A) AUTHORS: Aarts, Mark G.M.
          Keijzer, Christian J.
          Stiekema, Willem J.
          Pereira, Andy
      (B) TITLE: Molecular characterization of the CER1 gene
          of Arabidopsis involved in epicuticular wax
          biosynthesis and pollen fertility
      (C) JOURNAL: Plant Cell
      (D) VOLUME: 7
      (E) ISSUE: 12
      (F) PAGES: 2115-2127
      (G) DATE: december-1995

-continued (K) RELEVANT RESIDUES IN SEQ ID NO: 2: FROM 1 TO 2132

(xi) SEQUENCE DESCRIPTION: SEQ ID NO: 2:

```
CGACGGTATA ATG GCC ACA AAA CCA GGA GTC CTC ACC GAT TGG CCT TGG        49
           Met Ala Thr Lys Pro Gly Val Leu Thr Asp Trp Pro Trp
            1               5                  10

ACA CCC CTC GGA AGT TTC AAG TAC ATC GTA ATA GCA CCA TGG GCT GTC        97
Thr Pro Leu Gly Ser Phe Lys Tyr Ile Val Ile Ala Pro Trp Ala Val
 15                  20                  25

CAT AGC ACA TAC AGG TTT GTG ACA GAT GAT CCA GAG AAG AGG GAT CTC       145
His Ser Thr Tyr Arg Phe Val Thr Asp Asp Pro Glu Lys Arg Asp Leu
 30                  35                  40                  45

GGG TAC TTC CTT GTG TTC CCC TTC TTG CTC TTC AGA ATT CTG CAC AAC       193
Gly Tyr Phe Leu Val Phe Pro Phe Leu Leu Phe Arg Ile Leu His Asn
                 50                  55                  60

CAG GTT TGG ATC TCT CTG TCC CGT TAC TAT ACG TCC TCG GGA AAG AGA       241
Gln Val Trp Ile Ser Leu Ser Arg Tyr Tyr Thr Ser Ser Gly Lys Arg
             65                  70                  75

CGC ATC GTC GAC AAG GGA ATC GAC TTC AAT CAG GTC GAC AGG GAG ACC       289
Arg Ile Val Asp Lys Gly Ile Asp Phe Asn Gln Val Asp Arg Glu Thr
         80                  85                  90

AAC TGG GAT GAC CAA ATA TTG TTC AAC GGA GTG CTG TTC TAT ATA GGC       337
Asn Trp Asp Asp Gln Ile Leu Phe Asn Gly Val Leu Phe Tyr Ile Gly
     95                 100                 105

ATC AAC CTA TTG CCG GAG GCC AAA CAA CTT CCC TGG TGG AGA ACT GAC       385
Ile Asn Leu Leu Pro Glu Ala Lys Gln Leu Pro Trp Trp Arg Thr Asp
110                 115                 120                 125

GGA GTG TTG ATG GCA GCG CTT ATT CAC ACC GGA CCG GTG GAG TTC CTC       433
Gly Val Leu Met Ala Ala Leu Ile His Thr Gly Pro Val Glu Phe Leu
                130                 135                 140

TAT TAT TGG CTC CAC AAA GCT CTC CAC CAT CAC TTT CTT TAT TCC CGC       481
Tyr Tyr Trp Leu His Lys Ala Leu His His His Phe Leu Tyr Ser Arg
            145                 150                 155

TAC CAT TCC CAC CAC CAC TCC TCT ATC GTC ACT GAG CCC ATC ACT TCG       529
Tyr His Ser His His His Ser Ser Ile Val Thr Glu Pro Ile Thr Ser
        160                 165                 170

GTG ATA CAT CCG TTT GCG GAG CAC ATA GCA TAC TTC ATC CTC TTC GCG       577
Val Ile His Pro Phe Ala Glu His Ile Ala Tyr Phe Ile Leu Phe Ala
    175                 180                 185

ATA CCA CTA CTT ACC ACG TTG CTA ACA AAA ACG GCG TCA ATA ATT TCG       625
Ile Pro Leu Leu Thr Thr Leu Leu Thr Lys Thr Ala Ser Ile Ile Ser
190                 195                 200                 205

TTC GCC GGA TAC ATA ATC TAC ATA GAC TTC ATG AAC AAC ATG GGA CAC       673
Phe Ala Gly Tyr Ile Ile Tyr Ile Asp Phe Met Asn Asn Met Gly His
                210                 215                 220

TGC AAC TTC GAG CTA ATC CCT AAG CGC CTT TTC CAC CTC TTT CCT CCC       721
Cys Asn Phe Glu Leu Ile Pro Lys Arg Leu Phe His Leu Phe Pro Pro
            225                 230                 235

CTC AAG TTC CTC TGT TAC ACC CCC TCA TAC CAC TCG CTG CAC CAC ACG       769
Leu Lys Phe Leu Cys Tyr Thr Pro Ser Tyr His Ser Leu His His Thr
        240                 245                 250

CAG TTC CGG ACC AAC TAC TCC CTC TTC ATG CCC TTG TAT GAC TAC ATC       817
Gln Phe Arg Thr Asn Tyr Ser Leu Phe Met Pro Leu Tyr Asp Tyr Ile
    255                 260                 265

TAC GGC ACA ATG GAT GAA AGC ACG GAT ACG TTG TAC GAG AAA ACT CTA       865
Tyr Gly Thr Met Asp Glu Ser Thr Asp Thr Leu Tyr Glu Lys Thr Leu
270                 275                 280                 285

GAA AGA GGA GAT GAT AGA GTG GAC GTG GTG CAC TTA ACT CAC CTG ACG       913
Glu Arg Gly Asp Asp Arg Val Asp Val Val His Leu Thr His Leu Thr
                290                 295                 300
```

```
ACG CCA GAA TCC ATA TAC CAT TTG CGC ATT GGC TTG GCC TCA TTT GCC          961
Thr Pro Glu Ser Ile Tyr His Leu Arg Ile Gly Leu Ala Ser Phe Ala
            305                 310                 315

TCC TAC CCC TTC GCT TAT AGA TGG TTC ATG CGC CTT TTG TGG CCT TTC         1009
Ser Tyr Pro Phe Ala Tyr Arg Trp Phe Met Arg Leu Leu Trp Pro Phe
            320                 325                 330

ACC TCT CTC TCC ATG ATA TTC ACG CTC TTC TAC GCC CGC CTC TTT GTC         1057
Thr Ser Leu Ser Met Ile Phe Thr Leu Phe Tyr Ala Arg Leu Phe Val
            335                 340                 345

GCT GAG AGA AAC TCC TTC AAC AAG CTC AAC TTG CAG TCT TGG GTG ATA         1105
Ala Glu Arg Asn Ser Phe Asn Lys Leu Asn Leu Gln Ser Trp Val Ile
350                 355                 360                 365

CCT AGA TAT AAT CTA CAG TAC TTG TTA AAA TGG AGG AAA GAA GCG ATC         1153
Pro Arg Tyr Asn Leu Gln Tyr Leu Leu Lys Trp Arg Lys Glu Ala Ile
            370                 375                 380

AAT AAC ATG ATT GAG AAA GCG ATA CTG GAG GCA GAT AAG AAA GGA GTG         1201
Asn Asn Met Ile Glu Lys Ala Ile Leu Glu Ala Asp Lys Lys Gly Val
            385                 390                 395

AAG GTG CTT AGT CTG GGT CTC ATG AAC CAA GGG GAG GAG CTT AAC AGG         1249
Lys Val Leu Ser Leu Gly Leu Met Asn Gln Gly Glu Glu Leu Asn Arg
            400                 405                 410

AAC GGA GAG GTG TAT ATC CAC AAC CAT CCA GAT ATG AAA GTG AGA CTG         1297
Asn Gly Glu Val Tyr Ile His Asn His Pro Asp Met Lys Val Arg Leu
            415                 420                 425

GTC GAC GGC AGT AGA TTA GCA GCA GCT GTT GTG ATC AAC AGT GTA CCC         1345
Val Asp Gly Ser Arg Leu Ala Ala Ala Val Val Ile Asn Ser Val Pro
430                 435                 440                 445

AAA GCA ACT ACA AGC GTC GTG ATG ACA GGC AAT CTC ACT AAG GTT GCC         1393
Lys Ala Thr Thr Ser Val Val Met Thr Gly Asn Leu Thr Lys Val Ala
            450                 455                 460

TAC ACC ATC GCC TCT GCT CTC TGC CAG AGA GGC GTT CAG GTC TCC ACT         1441
Tyr Thr Ile Ala Ser Ala Leu Cys Gln Arg Gly Val Gln Val Ser Thr
            465                 470                 475

CTG CGC CTA GAC GAG TAT GAG AAA ATA AGA TCA TGC GTT CCA CAA GAA         1489
Leu Arg Leu Asp Glu Tyr Glu Lys Ile Arg Ser Cys Val Pro Gln Glu
            480                 485                 490

TGC AGA GAC CAT TTG GTC TAT TTA ACC TCT GAA GCA CTC TCA TCA AAC         1537
Cys Arg Asp His Leu Val Tyr Leu Thr Ser Glu Ala Leu Ser Ser Asn
495                 500                 505

AAG GTA TGG CTG GTG GGA GAA GGA ACA ACA AGA GAA GAG CAG GAA AAA         1585
Lys Val Trp Leu Val Gly Glu Gly Thr Thr Arg Glu Glu Gln Glu Lys
510                 515                 520                 525

GCC ACA AAA GGG ACA TTG TTT ATA CCA TTC TCA CAG TTC CCC CTC AAG         1633
Ala Thr Lys Gly Thr Leu Phe Ile Pro Phe Ser Gln Phe Pro Leu Lys
            530                 535                 540

CAG TTA CGT AGC GAT TGT ATC TAT CAT ACC ACA CCA GCA TTG ATA GTT         1681
Gln Leu Arg Ser Asp Cys Ile Tyr His Thr Thr Pro Ala Leu Ile Val
            545                 550                 555

CCA AAA TCT CTG GTG AAT GTC CAC TCC TGT GAG AAC TGG TTA CCG AGA         1729
Pro Lys Ser Leu Val Asn Val His Ser Cys Glu Asn Trp Leu Pro Arg
            560                 565                 570

AAG GCG ATG AGT GCA ACT AGA GTG GCC GGC ATA TTG CAC GCC TTA GAA         1777
Lys Ala Met Ser Ala Thr Arg Val Ala Gly Ile Leu His Ala Leu Glu
            575                 580                 585

GGA TGG GAA ACG CAT GAG TGT GGC ACA TCC CTT CTT CTC TCG GAT TTG         1825
Gly Trp Glu Thr His Glu Cys Gly Thr Ser Leu Leu Leu Ser Asp Leu
590                 595                 600                 605

GAC AAA GTA TGG GAA GCC TGT CTC AGC CAC GGC TTC CAG CCT CTC CTC         1873
Asp Lys Val Trp Glu Ala Cys Leu Ser His Gly Phe Gln Pro Leu Leu
```

-continued

```
                     610                 615                 620
CTT CCA CAT CAT TAAAACTCCA ACCTTGGAAG ATTTTTGGAG AATGAGAGCG        1925
Leu Pro His His
            625

ACACGCTCTG TGCTTCTTTT CCTTATGATC CAGCTCTTCC ACGCACACAT GAACTATGAA  1985

ACATATATAA AGCGCACACA TTTTATGTTT TACGCACACA TATATTTATG CATATCAAGC  2045

TTTTGGTGAT TATGGTATTG ATAGAGTCAA ATTAAGCTCG GTGACTATGG TATTAATAAG  2105

AGTACTATTT CCTTAAAAAA AAAAAAA                                      2132
```

(2) INFORMATION FOR SEQ ID NO: 3:

(i) SEQUENCE CHARACTERISTICS:
        (A) LENGTH: 625 amino acids
        (B) TYPE: amino acid
        (D) TOPOLOGY: linear (ii) MOLECULE TYPE: protein (xi) SEQUENCE DESCRIPTION: SEQ ID NO: 3:

```
Met Ala Thr Lys Pro Gly Val Leu Thr Asp Trp Pro Trp Thr Pro Leu
 1               5                  10                  15

Gly Ser Phe Lys Tyr Ile Val Ile Ala Pro Trp Ala Val His Ser Thr
                20                  25                  30

Tyr Arg Phe Val Thr Asp Asp Pro Glu Lys Arg Asp Leu Gly Tyr Phe
            35                  40                  45

Leu Val Phe Pro Phe Leu Leu Phe Arg Ile Leu His Asn Gln Val Trp
        50                  55                  60

Ile Ser Leu Ser Arg Tyr Tyr Thr Ser Ser Gly Lys Arg Arg Ile Val
 65                  70                  75                  80

Asp Lys Gly Ile Asp Phe Asn Gln Val Asp Arg Glu Thr Asn Trp Asp
                85                  90                  95

Asp Gln Ile Leu Phe Asn Gly Val Leu Phe Tyr Ile Gly Ile Asn Leu
            100                 105                 110

Leu Pro Glu Ala Lys Gln Leu Pro Trp Trp Arg Thr Asp Gly Val Leu
        115                 120                 125

Met Ala Ala Leu Ile His Thr Gly Pro Val Glu Phe Leu Tyr Tyr Trp
    130                 135                 140

Leu His Lys Ala Leu His His Phe Leu Tyr Ser Arg Tyr His Ser
145                 150                 155                 160

His His His Ser Ser Ile Val Thr Glu Pro Ile Thr Ser Val Ile His
                165                 170                 175

Pro Phe Ala Glu His Ile Ala Tyr Phe Ile Leu Phe Ala Ile Pro Leu
            180                 185                 190

Leu Thr Thr Leu Leu Thr Lys Thr Ala Ser Ile Ser Phe Ala Gly
        195                 200                 205

Tyr Ile Ile Tyr Ile Asp Phe Met Asn Asn Met Gly His Cys Asn Phe
    210                 215                 220

Glu Leu Ile Pro Lys Arg Leu Phe His Leu Phe Pro Pro Leu Lys Phe
225                 230                 235                 240

Leu Cys Tyr Thr Pro Ser Tyr His Ser Leu His His Thr Gln Phe Arg
                245                 250                 255

Thr Asn Tyr Ser Leu Phe Met Pro Leu Tyr Asp Tyr Ile Tyr Gly Thr
            260                 265                 270

Met Asp Glu Ser Thr Asp Thr Leu Tyr Glu Lys Thr Leu Glu Arg Gly
        275                 280                 285
```

```
Asp Asp Arg Val Asp Val Val His Leu Thr His Leu Thr Thr Pro Glu
    290                 295                 300

Ser Ile Tyr His Leu Arg Ile Gly Leu Ala Ser Phe Ala Ser Tyr Pro
305                 310                 315                 320

Phe Ala Tyr Arg Trp Phe Met Arg Leu Leu Trp Pro Phe Thr Ser Leu
                325                 330                 335

Ser Met Ile Phe Thr Leu Phe Tyr Ala Arg Leu Phe Val Ala Glu Arg
            340                 345                 350

Asn Ser Phe Asn Lys Leu Asn Leu Gln Ser Trp Val Ile Pro Arg Tyr
        355                 360                 365

Asn Leu Gln Tyr Leu Leu Lys Trp Arg Lys Glu Ala Ile Asn Asn Met
    370                 375                 380

Ile Glu Lys Ala Ile Leu Glu Ala Asp Lys Lys Gly Val Lys Val Leu
385                 390                 395                 400

Ser Leu Gly Leu Met Asn Gln Gly Glu Glu Leu Asn Arg Asn Gly Glu
                405                 410                 415

Val Tyr Ile His Asn His Pro Asp Met Lys Val Arg Leu Val Asp Gly
            420                 425                 430

Ser Arg Leu Ala Ala Ala Val Val Ile Asn Ser Val Pro Lys Ala Thr
        435                 440                 445

Thr Ser Val Val Met Thr Gly Asn Leu Thr Lys Val Ala Tyr Thr Ile
    450                 455                 460

Ala Ser Ala Leu Cys Gln Arg Gly Val Gln Val Ser Thr Leu Arg Leu
465                 470                 475                 480

Asp Glu Tyr Glu Lys Ile Arg Ser Cys Val Pro Gln Glu Cys Arg Asp
                485                 490                 495

His Leu Val Tyr Leu Thr Ser Glu Ala Leu Ser Ser Asn Lys Val Trp
            500                 505                 510

Leu Val Gly Glu Gly Thr Thr Arg Glu Glu Gln Glu Lys Ala Thr Lys
        515                 520                 525

Gly Thr Leu Phe Ile Pro Phe Ser Gln Phe Pro Leu Lys Gln Leu Arg
    530                 535                 540

Ser Asp Cys Ile Tyr His Thr Thr Pro Ala Leu Ile Val Pro Lys Ser
545                 550                 555                 560

Leu Val Asn Val His Ser Cys Glu Asn Trp Leu Pro Arg Lys Ala Met
                565                 570                 575

Ser Ala Thr Arg Val Ala Gly Ile Leu His Ala Leu Glu Gly Trp Glu
            580                 585                 590

Thr His Glu Cys Gly Thr Ser Leu Leu Leu Ser Asp Leu Asp Lys Val
        595                 600                 605

Trp Glu Ala Cys Leu Ser His Gly Phe Gln Pro Leu Leu Leu Pro His
    610                 615                 620

His
625

(2) INFORMATION FOR SEQ ID NO: 4:

(i) SEQUENCE CHARACTERISTICS:
        (A) LENGTH: 1644 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (vi) ORIGINAL SOURCE:
         (A) ORGANISM: Arabidopsis thaliana
         (B) STRAIN: Landsberg erecta ecotype (vii) IMMEDIATE SOURCE:
         (A) LIBRARY: Coates (viii) POSITION IN GENOME:
         (A) CHROMOSOME/SEGMENT: 1
         (B) MAP POSITION: 12
         (C) UNITS: cM (x) PUBLICATION INFORMATION:
         (A) AUTHORS: Aarts, Mark G.M.
             Keijzer, Christian J.
             Stiekema, Willem J.
             Pereira, Andy
         (B) TITLE: Molecular characterization of the CER1 gene
             of Arabidopsis involved in epicuticular wax
             biosynthesis and pollen fertility
         (C) JOURNAL: Plant Cell
         (D) VOLUME: 7
         (E) ISSUE: 12
         (F) PAGES: 2115-2127
         (G) DATE: december-1995
         (K) RELEVANT RESIDUES IN SEQ ID NO: 4: FROM 1 TO 750

(xi) SEQUENCE DESCRIPTION: SEQ ID NO: 4:

```
CGTCAAGGTT TGTGAATATA TGAGGGAATT GGATATATAT ACTCAGCTTC TCATATCAAA      60

CAAAAAATAA TGTAGTAATG TGTATATATA GGTGGTCGTG TTACGCGAGG AGGAACACAG     120

CAAACTCATC AAATCTGGGG TTGACAAGAA TCTGGTACTG TCTACAAGCA ATAGTTATTA     180

CTCCCCAAAG GTGTGGTTGG TGGGGATGG AATAGAGAAC GAAGAGCAGA TGAAAGCAAA      240

AGAAGGAACC CTCTTTGTTC CCTTTTCTCA CTTTCCGCCC AACAAACTCC GCAAGGACTG     300

TTTCTACCAG TCCACTCCAG CTATGCGTGT TCCCAAGTCT GCCCAAAACA TCGACTCCTG     360

TGAGGTACAT CTTTGAATTC TTATAGATAT ATCTGTAACT TTTATATTAT ATAAGCTGAT     420

AGATGTGTTC ATCTATAATG AATGAATGGT TGTTATATAT ATATAGAACT GGCTGGGGAG     480

GAGGGTGATG AGTGCATGGA AAATAGGAGG TATAGTGCAT GCACTTGAGG GTTGGGAGGA     540

GCATGACTGC GGCAACACTT GCAACGTCCT CCGTCTCCAC GCCATATGGG AAGCTGCTCT     600

TCGCCATGAT TTCAACCTC TCCCACCATC TCCTCTATGA GCTTTTTTCA TATTCATACA      660

TCTATGTCCC CTTTCTTGAT TATATCTACT TCCCTTCCAT CATTGTTGCT GTTACTATGT     720

TTTCTATCGA CAATATATAA GTACCCTTGT TACCCTTGGT GCACGTGCTT CATATATGTT     780

AGAAGGGCAA AAAATTCGTC GTATGATATG CTTAGTTAAA TTTTATAAAA CTCAATAAAA     840

ATCTTCAGAA ACAGTGCTAT GATCATTACA TCTTAACTAA GTGATATATA TCTGCGTGCC     900

TATTTAACAA AATAAACAAA AAAACAAAAC AAAATATATT TGGGTGCATC ATCAAATCAA     960

AGTAGTTGCA AAAACTGGAC GAGGTTTTTA CTTAAATGGT CCTTACCCCG CATGGTCCAC    1020

TTGCTACCTA ATTAAGGATT GGTAGGGTGC GTATACGTAT ATAAATTGTG GCGGTGGGAG    1080

ATGGAGTTAC TAAAAACGAA ACGTACAAGT ATTATTCATA GCTCTCGTAT AAGGGGTTAG    1140

TCCTTAGATC TAGATATTTT CACTTTTCTT TCATTTATGT CGGAGCAACA GACACTAGCT    1200

GGCGCTTCAA CGTGCATGAT CTTGATTGGC TAGTAAATTC CAAGCATCAA TACCTAACAC    1260

ATGCCCAACT TGGTTCATTA GTATTCTTTC ATTGGTAAAA TACCCTTACC TTTCAATAAT    1320

ATCCAGAAAT AAATATATGA AGCCATCCAT CAACCGGTGC ATTTCCTCAA GGCATGGATA    1380

TGATATCAGA ACATCGATGA AGGTGGGAGG GGGTAATTAG CTGAGTGTCA TAAATGAGGA    1440
```

```
TCCATGTGGA GATCATCGAA TGGTAGTAGT ACATGTTTGG TCTTAGCTGG CCCCACCACA      1500

AGGAATTGGA CTGGTGGGAA GATAGGGGTG GGTTACGTCA TTCCACATAT CTACCAATTA      1560

AGGAGTTTAA TATAAACCTT GCTATATAAT GTACCTTGGC TCACAAGAGT TGAAGAGACA      1620

CAGTGACGAC ACAAACATAT TACA                                             1644
```

(2) INFORMATION FOR SEQ ID NO: 5:

(i) SEQUENCE CHARACTERISTICS:
        (A) LENGTH: 625 amino acids
        (B) TYPE: amino acid
        (C) STRANDEDNESS:
        (D) TOPOLOGY: linear (ii) MOLECULE TYPE: protein (iii) HYPOTHETICAL: YES (vi) ORIGINAL SOURCE:
        (A) ORGANISM: Arabidopsis thaliana
        (B) STRAIN: Columbia ecotype
        (D) DEVELOPMENTAL STAGE: light and dark grown seedlings;
            rosette and whole plants (vii) IMMEDIATE SOURCE:
        (A) LIBRARY: PRL2

(ix) FEATURE:
        (A) NAME/KEY: Protein
        (B) LOCATION:1..625

(x) PUBLICATION INFORMATION:
        (A) AUTHORS: Aarts, Mark G.M.
            Keijzer, Christian J.
            Stiekema, Willem J.
            Pereira, Andy
        (B) TITLE: Molecular characterization of the CER1 gene
            of Arabidopsis involved in epicuticular wax
            biosynthesis and pollen fertility
        (C) JOURNAL: Plant Cell
        (D) VOLUME: 7
        (E) ISSUE: 12
        (F) PAGES: 2115-2127
        (G) DATE: december-1995
        (K) RELEVANT RESIDUES IN SEQ ID NO: 5: FROM 1 TO 625

(xi) SEQUENCE DESCRIPTION: SEQ ID NO: 5:

```
Met Ala Thr Lys Pro Gly Val Leu Thr Asp Trp Pro Trp Thr Pro   Leu
1               5                   10                  15

Gly Ser Phe Lys Tyr Ile Val Ile Ala Pro Trp Ala Val His Ser   Thr
            20                  25                  30

Tyr Arg Phe Val Thr Asp Asp Pro Glu Lys Arg Asp Leu Gly Tyr   Phe
        35                  40                  45

Leu Val Phe Pro Phe Leu Leu Phe Arg Ile Leu His Asn Gln Val   Trp
    50                  55                  60

Ile Ser Leu Ser Arg Tyr Tyr Thr Ser Ser Gly Lys Arg Arg Ile Val
65                  70                  75                  80

Asp Lys Gly Ile Asp Phe Asn Gln Val Asp Arg Glu Thr Asn Trp Asp
            85                  90                  95

Asp Gln Ile Leu Phe Asn Gly Val Leu Phe Tyr Ile Gly Ile Asn Leu
            100                 105                 110

Leu Pro Glu Ala Lys Gln Leu Pro Trp Trp Arg Thr Asp Gly Val Leu
            115                 120                 125

Met Ala Ala Leu Ile His Thr Gly Pro Val Glu Phe Leu Tyr Tyr Trp
            130                 135                 140
```

```
Leu His Lys Ala Leu His His His Phe Leu Tyr Ser Arg Tyr His Ser
145                 150                 155                 160

His His His Ser Ser Ile Val Thr Glu Pro Ile Thr Ser Val Ile His
                165                 170                 175

Pro Phe Ala Glu His Ile Ala Tyr Phe Ile Leu Phe Ala Ile Pro Leu
            180                 185                 190

Leu Thr Thr Leu Leu Thr Lys Thr Ala Ser Ile Ile Ser Phe Ala Gly
        195                 200                 205

Tyr Ile Ile Tyr Ile Asp Phe Met Asn Asn Met Gly His Cys Asn Phe
    210                 215                 220

Glu Leu Ile Pro Lys Arg Leu Phe His Leu Phe Pro Pro Leu Lys Phe
225                 230                 235                 240

Leu Cys Tyr Thr Pro Ser Tyr His Ser Leu His His Thr Gln Phe Arg
                245                 250                 255

Thr Asn Tyr Ser Leu Phe Met Pro Leu Tyr Asp Tyr Ile Tyr Gly Thr
            260                 265                 270

Met Asp Glu Ser Thr Asp Thr Leu Tyr Glu Lys Thr Leu Glu Arg Gly
        275                 280                 285

Asp Asp Arg Val Asp Val His Leu Thr His Leu Thr Thr Pro Glu
    290                 295                 300

Ser Ile Tyr His Leu Arg Ile Gly Leu Ala Ser Phe Ala Ser Tyr Pro
305                 310                 315                 320

Phe Ala Tyr Arg Trp Phe Met Arg Leu Leu Trp Pro Phe Thr Ser Leu
                325                 330                 335

Ser Met Ile Phe Thr Leu Phe Tyr Ala Arg Leu Phe Val Ala Glu Arg
            340                 345                 350

Asn Ser Phe Asn Lys Leu Asn Leu Gln Ser Trp Val Ile Pro Arg Tyr
        355                 360                 365

Asn Leu Gln Tyr Leu Leu Lys Trp Arg Lys Glu Ala Ile Asn Asn Met
    370                 375                 380

Ile Glu Lys Ala Ile Leu Glu Ala Asp Lys Lys Gly Val Lys Val Leu
385                 390                 395                 400

Ser Leu Gly Leu Met Asn Gln Gly Glu Glu Leu Asn Arg Asn Gly Glu
                405                 410                 415

Val Tyr Ile His Asn His Pro Asp Met Lys Val Arg Leu Val Asp Gly
            420                 425                 430

Ser Arg Leu Ala Ala Ala Val Val Ile Asn Ser Val Pro Lys Ala Thr
        435                 440                 445

Thr Ser Val Val Met Thr Gly Asn Leu Thr Lys Val Ala Tyr Thr Ile
    450                 455                 460

Ala Ser Ala Leu Cys Gln Arg Gly Val Gln Val Ser Thr Leu Arg Leu
465                 470                 475                 480

Asp Glu Tyr Glu Lys Ile Arg Ser Cys Val Pro Gln Glu Cys Arg Asp
                485                 490                 495

His Leu Val Tyr Leu Thr Ser Glu Ala Leu Ser Ser Asn Lys Val Trp
            500                 505                 510

Leu Val Gly Glu Gly Thr Thr Arg Glu Glu Gln Glu Lys Ala Thr Lys
        515                 520                 525

Gly Thr Leu Phe Ile Pro Phe Ser Gln Phe Pro Leu Lys Gln Leu Arg
    530                 535                 540

Ser Asp Cys Ile Tyr His Thr Thr Pro Ala Leu Ile Val Pro Lys Ser
545                 550                 555                 560

Leu Val Asn Val His Ser Cys Glu Asn Trp Leu Pro Arg Lys Ala Met
```

```
            565                 570                 575
Ser Ala Thr Arg Val Ala Gly Ile Leu His Ala Leu Glu Gly Trp Glu
            580                 585                 590
Thr His Glu Cys Gly Thr Ser Leu Leu Leu Ser Asp Leu Asp Lys Val
        595                 600                 605
Trp Glu Ala Cys Leu Ser His Gly Phe Gln Pro Leu Leu Leu Pro His
    610                 615                 620
His
625
```

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 6:

GGCCTCCGGC AATAGGTTGA TG                                      22

(2) INFORMATION FOR SEQ ID NO: 7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 7:

GGAGCATGAG AATTGCAGAT ACC                                   23

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 8:

GGCGTCGTCA GGTGAGTTAA GTGC                                24

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 9:

GGTGCTTAGT CTGGGTCTCA TG                                      22

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 10:

CACAGGAGTG GACATTCACC AGAG                                24

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 11:

CGCATGAGTG TGGCACATCC C          21

(2) INFORMATION FOR SEQ ID NO: 12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 12:

GACACTCCTT AGATCTTTTC TTGTAGTG        28